United States Patent [19]
Horn et al.

[11] Patent Number: 6,017,700
[45] Date of Patent: Jan. 25, 2000

[54] CATIONIC OLIGONUCLEOTIDES, AND RELATED METHODS OF SYNTHESIS AND USE

[75] Inventors: Thomas Horn, Berkeley, Calif.; Robert L. Letsinger, Wilmette, Ill.; Tanjore N. Balasubramaniam, Madras, India

[73] Assignee: Bayer Corporation, East Walpole, Mass.

[21] Appl. No.: 08/693,831

[22] Filed: Jul. 31, 1996

Related U.S. Application Data

[60] Provisional application No. 60/001,901, Aug. 4, 1995, abandoned.

[51] Int. Cl.$^7$ .............................. C12Q 1/68; C07H 19/00; C07H 21/02; C07H 21/04
[52] U.S. Cl. ........................... 435/6; 536/22.1; 536/23.1; 536/24.3; 536/25.33; 536/25.4
[58] Field of Search .............................. 435/6; 536/22.1, 536/23.1, 24.3, 25.33, 25.4

[56] References Cited

U.S. PATENT DOCUMENTS

| | | | |
|---|---|---|---|
| 4,868,105 | 9/1989 | Urdea et al. | 435/6 |
| 4,958,013 | 9/1990 | Letsinger | 536/27 |
| 5,416,203 | 5/1995 | Letsinger | 536/25.34 |

FOREIGN PATENT DOCUMENTS

| | | |
|---|---|---|
| 0214908 | 3/1987 | European Pat. Off. . |
| WO 93/11148 | 6/1993 | WIPO . |

OTHER PUBLICATIONS

Chaturvedi et al., "Stabilization of triple–stranded oligonucleotide complexes: use of probes containing alternative phosphodiester and stero–uniform cationic phosphoramidate linkages," *Nuc. Acids Res.* (1996)24:(12)2318–2323.

Fathi et al., "Oligonucleotides with novel, catonic backbone substituents: aminoethylphosphonates," *Nucleic Acids Res.* (1994)22:5416–5424.

Fathi et al., "(Aminomethyl) phosphonate derivatives of oligonucleotides," *Bioconjugate Chem.* (1994)5:47–57.

Horn et al., "Oligonucleotides and alternating anionic and cationic phosphoramidate linkages: synthesis and hybridization of stereo–uniform isomers," *Tetrahedron Ltrs.* (1996)37(6):743–746.

Letsinger et al., "Cationic Oligonucleotides," *J. Am. Chem. Soc.* (1988) 110:470–4471.

Patil et al., "Syntheses and properties of oligothymidylate analogs containing stereoregulated phosphorothioate and phosphodiester linkages in an alternating manner," *Bioorganic & Med. Chem. Ltrs.,* (1994)4(22):2663–2666.

Peyrottes et al., "Synthesis, base pairing properties and nuclease resistance of oligothymidylate analogs containing methoxyphosphoramidate internucleoside linkages," *Nucleosides & Nucleotides,* (1994)13(10):2135–2149.

Cook et al., "Synthesis and Properties of Oligonucleotide (2–Aminoethyl) Phosphates," *Nucleosides & Nucleotides* 14(3–5):1005–1008 (1995).

Danilyuk et al., "Positively Charged Analogs of Oligonucleotides. Synthesis of Aminohexyl Triester Derivatives of Oligothymidlylates and Study of their Complex–Forming Properties," *CA* 95(15):133293.

Marshall et al., "Phosphorodithioate DNA as a Potential Therapeutic Drug," *Science* 259:1564–1570 (1993).

Seliger et al., "Specific Intrachain Introduction of Reporter Groups into Oligonucleotides as Substituents at Internucleotidic Linkages," *Nucleosides & Nucleotides* 10(1–3):303–306 (1991).

Sobkowski et al., "Studies on Reactions of Nucleoside H–Phosphonate Diesters with Bifunctional Reagents, Part 4. Chemoselectivity During Oxidative Coupling of Nucleoside H–Phosphonate Diesters with Amino Alcohols Controlled by Protonation of the Amino Function," *Tetrahedron Letters* 36(13):2295–2298 (1995).

Stein et al. "Phosphorothioate Oligodeoxynucleotides. Antisense Inhibitors of Gene Expression?" *CA* 117(13):123838.

*Primary Examiner*—Ardin H. Marschel
*Assistant Examiner*—Jezia Riley

[57] ABSTRACT

Novel oligonucleotides are provided having cationic internucleoside linkages. The cationic internucleoside linkage has the structure

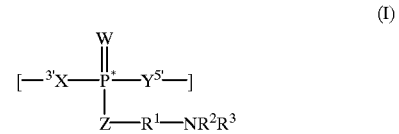
(I)

wherein W, X, Y, Z, $R^1$, $R^2$, and $R^3$ are as defined herein, P* represents an asymmetric phosphorus atom capable of existing in two distinct stereoisomeric configurations, and further wherein the internucleoside linkage is stereouniform. Certain of these oligonucleotides may have alternating anionic and cationic internucleoside linkages, which are not necessarily stereouniform. A method for synthesizing the compounds are provided as well, as are methods for using the compounds, e.g., as antisense molecules and in nucleic acid hybridization assays.

36 Claims, No Drawings

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<221> NAME/KEY: Description of Artificial Sequence: poly-T

<400> SEQUENCE: 1
tttttttttt ttttt                                                    15

CATIONIC OLIGONUCLEOTIDES, AND RELATED METHODS OF SYNTHESIS AND USE

CROSS-REFERENCE TO RELATED APPLICATION

This application is related to provisional patent application Ser. No. 60/001,901, filed Aug. 4, 1995, abandoned, from which priority is claimed under 35 USC §119(e) (1) and which is incorporated herein by reference in its entirety.

TECHNICAL FIELD

This invention relates generally to nucleic acid chemistry. More particularly, the invention relates to oligonucleotides containing cationic internucleoside linkages. In addition, the invention relates to methods and reagents for preparing such oligonucleotides. The invention has applications in antisense therapeutics and in nucleic acid hybridization assays for diagnostic or clinical monitoring purposes.

BACKGROUND

Sequence-specific oligonucleotides containing modified internucleoside phosphodiester linkages have utility as antisense molecules for therapeutic applications and nucleic acid hybridization probes for diagnostic or therapeutic efficacy-monitoring applications.

Successful antisense molecules and nucleic acid hybridization probes must bind specifically to the single-stranded or double-stranded target nucleic acid sequence of interest under physiological conditions. Such molecules and probes must also be effectively taken up by intact cells and must be resistant to nuclease degradation.

The phosphodiester backbone has been modified in an attempt to satisfy these criteria. For example, the phosphodiester backbone has been replaced by phosphonate (Miller et al. (1980) *J. Biol. Chem.* 255:9659–9665), phosphotriester (Pless et al. (1977) *Biochemistry* 16:1239–1250) or phosphorothioate backbones (Stec et al. (1984) *J. Am. Chem. Soc.* 106:6077–6079).

One approach to oligonucleotide backbone modification has been to remove the negative charge of the internucleoside phosphodiester ("PDE") linkage to produce neutral backbones such as, for example, methyl phosphonates (Vyazovkina et al. (1994) *Nucleic Acids Res.* 22:2404–2409), phosphoramidates (Jäger et al. (1988) *Biochemistry* 27:7237–7246) or peptide nucleic acids (Egholm et al. (1992) *J. Am. Chem. Soc.* 114:1895–1897).

An alternative approach to modifying the oligonucleotide backbone has been to replace anionic PDE groups with cationic groups. Cationic substituents have been attached to the internucleoside phosphorus atom via phosphoramidate linkages (Letsinger et al. (1988) *J. Am. Chem. Soc.* 110:4470–4471). Cationic groups can also be introduced into oligonucleotides via phosphonate derivatives in which the anionic oxygen is replaced by a cationic group via a phosphorus-carbon bond. Thus, the preparation of oligonucleotides in which the backbone consists of alternating phosphodiester and stereoisomerically pure (2-aminoethyl)-phosphonate linkages, and oligonucleotide containing backbones consisting of (aminomethyl)-phosphonates have been respectively reported in Fathi et al. (1994) *Nucleic Acids Res.* 22:5416–5424 and Fathi et al. (1994) *Bioconjugate Chem.* 5:47–57.

Patil et al. (1994) *Biorg. Medicinal Chem. Lett.* 4:2663–2666 reported the synthesis of oligothymidylate analogs containing stereoisomers of phosphorothioates using stereoisomerically pure modified dinucleosides to synthesize decathymidylates with alternating stereoregulated anionic phosphorothioate and anionic PDE linkages.

Peyrottes et al. (1994) *Nucleosides & Nucleotides* 13:2135–2149 prepared oligomers with methoxyphosphoramidate internucleoside linkages using preformed dimers. Furthermore, when compared with oligo(dT), the oligomer with the methoxyphosphoramidate internucleoside linkages showed reduced thermal stability when hybridized to poly (dA) or poly(A).

There is a need in the art for oligonucleotides having cationic internucleoside linkages that have greater affinity target nucleic acids than oligonucleotides having exclusively standard phosphodiester internucleoside linkages. Such oligonucleotides can serve as antisense therapeutic agents and as probes in nucleic acid hybridization assays.

SUMMARY OF THE INVENTION

Accordingly, it is an object of the invention to provide an oligonucleotide having cationic internucleoside linkages useful in antisense therapeutics and in nucleic acid hybridization assays for diagnostic or clinical monitoring purposes.

It is another aspect of the invention to provide a method of synthesizing oligonucleotides containing cationic internucleoside linkages.

It is yet another object of the invention to provide nucleic acid hybridization assays using oligonucleotide probes containing cationic internucleoside linkages.

In one embodiment of the invention, an oligonucleotide is provided having a cationic internucleoside linkage having the structure (I)

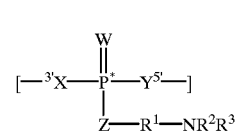

wherein:
W is selected from the group consisting of O, S and Se;
X and Y are independently selected from the group consisting of O, S, $C(R^4)R^5$ where $R^4$ and $R^5$ are independently selected from the group consisting of H and $C_1$–$C_6$ alkyl, and $NR^6$ where $R^6$ is H or $C_1$–$C_6$ alkyl;
Z is selected from the group consisting of O, S, $C_1$–$C_6$ alkylene, $C_2$–$C_6$ alkenylene, $C_2$–$C_6$ alkynylene and $NR^7$ where $R^7$ is H or $C_1$–$C_6$ alkyl, with the proviso that when W, X and Y are O, Z is O, S or $NR^7$;
$R^1$ is selected from the group consisting of $C_1$–$C_6$ alkylene, $C_2$–$C_6$ alkenylene, $C_2$–$C_6$ alkynylene, monocyclic arylene and a bond;
$R^2$ and $R^3$ are independently selected from the group consisting of H, $C_1$–$C_6$ alkyl, $C_1$–$C_6$ alkyl substituted with 1 to 4 $NH_2$ groups, and monocyclic aryl, or $R^2$ and $R^3$ may be linked to form a five- or six-membered alkyl or aryl ring or an N-, O- or S-containing heterocycle; and
wherein P* represents an asymmetric phosphorus atom capable of existing in two distinct stereoisomeric configurations,
and further wherein the linkage is stereouniform.

In another embodiment of the invention, an oligonucleotide is provided having alternating cationic and anionic internucleoside linkages wherein the cationic internucleoside linkages have the structure (II)

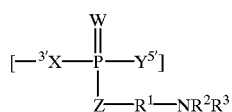
(II)

wherein W, X, Y, Z, $R^1$, $R^2$ and $R^3$ are as defined above, with the proviso that when W, X and Y are O, Z is O or S, and wherein P is a phosphorus atom that may or may not be capable of existing in two distinct stereoisomeric configurations, and further wherein the linkage may or may not be stereouniform.

In still another embodiment of the invention, an oligonucleotide is provided having at least one cationic internucleoside linkage having the structure (II)

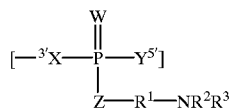
(II)

wherein W, X, Y, Z, $R^1$, $R^2$ and $R^3$ are as defined above, with the proviso that when W, X and Y are O, Z is O or S.

In a further embodiment of the invention, a method is provided for making an oligonucleotide containing at least one cationic internucleoside linkage having the structure (I)

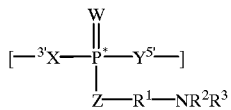
(I)

wherein:
W is selected from the group consisting of O, S and Se;
X and Y are independently selected from the group consisting of O, S, $C(R^4)R^5$ where $R^4$ and $R^5$ are independently selected from the group consisting of H and $C_1$–$C_6$ alkyl, and $NR^6$ where $R^6$ is H or $C_1$–$C_6$ alkyl;
Z is selected from the group consisting of O, S, $C_1$–$C_6$ alkylene, $C_2$–$C_6$ alkenylene, $C_2$–$C_6$ alkynylene and $NR^7$ where $R^7$ is H or $C_1$–$C_6$ alkyl, with the proviso that when W, X and Y are O, Z is O, S or $NR^7$;
$R^1$ is selected from the group consisting of $C_1$–$C_6$ alkylene, $C_2$–$C_6$ alkenylene, $C_2$–$C_6$ alkynylene, monocyclic arylene and a bond;
$R^2$ and $R^3$ are independently selected from the group consisting of H, $C_1$–$C_6$ alkyl, $C_1$–$C_6$ alkyl substituted with 1 to 4 $NH_2$ groups, and monocyclic aryl, or $R^2$ and $R^3$ may be linked to form a five- or six-membered alkyl or aryl ring or an N-, O- or S-containing heterocycle; and
wherein P* represents an asymmetric phosphorus atom capable of existing in two distinct stereoisomeric configurations, and further wherein the linkage is stereouniform, said method comprising:
(a) synthesizing a point racemic mixture of protected cationic nucleotide dimers comprising the cationic internucleoside linkage and a 3'—O—TBDMS protecting group;
(b) optionally resolving the stereoisomers in the mixture;
(c) deprotecting the cationic nucleotide dimer isolated in step (b);
(d) converting the deprotected cationic nucleotide dimer provided in step (c) into the corresponding 3'—O—$CH_2CH_2CN$ phosphoramidite derivative by reaction with Cl—$P(N(iPr)_2)$—O—BCE; and
(e) coupling the 3'—O—$CH_2CH_2CN$ phosphoramidite derivative to an unprotected hydroxyl-containing terminal unit of an oligonucleotide chain.

In yet another embodiment of the invention, a nucleic acid hybridization assay is provided comprising:
(a) providing a labeled oligonucleotide probe containing at least one cationic internucleoside linkage;
(b) hybridizing the probe to a single-stranded analyte nucleic acid to produce a labeled duplex; and
(c) detecting the labeled duplexes.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

Definitions and nomenclature:

Before the present invention is disclosed and described in detail, it is to be understood that this invention is not limited to specific assay formats, materials or reagents, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to an oligonucleotide containing "a cationic internucleoside linkage" includes polynucleotides containing two or more cationic internucleoside linkages and the like.

In this specification and in the claims which follow, reference will be made to a number of terms which shall be defined to have the following meanings:

As used herein, the terms "polynucleotide" and "oligonucleotide" shall be generic to polydeoxyribonucleotides (containing 2'-deoxy-D-ribose), to polyribonu-cleotides (containing D-ribose), to any other type of polynucleotide which is an N- or C-glycoside of a purine or pyrimidine base, and to other polymers containing nonnucleotidic backbones, for example, polyamide (e.g., peptide nucleic acids (PNAs)) and polymorpholino (commercially available from the Anti-Virals, Inc., Corvallis, Oreg., as Neugene™ polymers), and other synthetic sequence-specific nucleic acid polymers providing that the polymers contain nucleobases in a configuration which allows for base pairing and base stacking, such as is found in DNA and RNA. There is no intended distinction in length between the term "polynucleotide" and "oligonu-cleotide," and these terms will be used interchangeably. These terms refer only to the primary structure of the molecule. Thus, these terms include double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.) and with negatively charged linkages (e.g., phosphorothioates, phosphorodi-thioates, etc.), those containing 2'—O— internucleotide linkages of 3'-oxy or 3'-deoxy ribose moieties, those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. In addition, the terms "nucleoside" and "nucleotide" include those moieties which contain not only conventional ribose and deoxyribose sugars, but also other sugars as well. Modified nucleosides or nucleotides will also include modifications on the sugar moiety, e.g., wherein one or more of the hydroxyl groups are replaced with halogen, aliphatic groups, or are functionalized as ethers, amines, or the like.

The designation "3'" as used in a structural representation of an internucleoside linkage refers to a bond to the 3' carbon of the ribose moiety of the nucleoside situated 5' to the linkage. The designation "5'" as used in a structural representation of an internucleoside linkage refers to a bond to the 5' carbon of the ribose moiety of the nucleoside situated 3' to the linkage. However, as indicated above, the invention is not intended to be limited to oligonucleotides including ribose sugars as part of the backbone. Accordingly, one of ordinary skill in the art would know that the novel oligonucleotides containing cationic internucleoside linkages as depicted herein need not be limited to traditional 3' and 5' internucleoside bonds.

The term "cationic" as used herein refers to a chemical moiety that carries a positive charge at pH less than about 9, preferably less than about 8. More preferably, when in an aqueous solution near neutrality, i.e., in the range of about pH 4 to pH 8, preferably about pH 7, most preferably about pH 7.3, a cationic moiety will be protonated to carry a positive charge. Thus, a "cationic internucleoside linkage" is such a linkage that includes a substituent chemical moiety that is positively charged under the above-described conditions. A "cationic oligonucleotide" is used herein to indicate an oligonucleotide having one or more cationic internucleoside linkages.

The term "alkyl" or "lower alkyl" as used herein refers to a branched or unbranched saturated hydrocarbon group of 1 to 6 carbon atoms, such as methyl, ethyl, n-propyl, isopropyl ("iPr"), n-butyl, isobutyl, t-butyl and the like. The term "alkylene" or "lower alkylene" as used herein refers to a bifunctional saturated branched or unbranched hydrocarbon chain containing from 1 to 6 carbon atoms, and includes, for example, methylene (—$CH_2$—), ethylene (—$CH_2$–$CH_2$—), propylene (—$CH_2$–$CH_2$–$CH_2$—), 2-methylpropylene [—$CH_2$ —CH($CH_3$)—$CH_2$—], hexylene [—$(CH_2)_6$—] and the like.

The term "alkenylene" or "lower alkenylene" as used herein refers to a bifunctional branched or unbranched hydrocarbon chain containing 2 to 6 carbon atoms and at least one double bond. The term "alkynylene" or "lower alkynylene" as used herein refers to a bifunctional branched or unbranched hydrocarbon chain containing 2 to 6 carbon atoms and at least one triple bond.

The term "aryl" as used herein refers to an aromatic species containing 1 to 5 aromatic rings, either unsubstituted or substituted with 1 or more substituents typically selected from the group consisting of halogen and $C_1$–$C_6$ alkyl.

The term "arylene" refers to a difunctional aromatic moiety; "monocyclic arylene" refers to a phenylene group. These groups may be substituted with up to four ring substituents as outlined above.

The term "heterocycle" is used in its conventional meaning to include substituted or unsubstituted aromatic and nonaromatic cyclic molecules containing heteroatoms such as O, N, S, P and halogens. Examples of such heterocycles include pyrrole, pyrrolidine, pyridine, piperidine, morpholine, quinoline, indole, pyrimidine, piperazine, pipecoline, imidazole, benzimidazole, purine and the like. These groups may also be substituted as outlined above.

By "purified" or "homogeneous" is meant, when referring to a polypeptide or nucleotide sequence that the indicated molecule is present in the substantial absence of other biological macromolecules of the same type or stereoisomeric configuration. The term "purified" or "homogeneous" as used herein preferably means at least about 90% by weight, more preferably at least about 95% by weight, and most preferably at least about 98% by weight, of biological macromolecules of the same type present.

The term "stereoisomer" is used in its conventional sense to refer to a chemical compound having at least one asymmetric atom such that the compound can exist in two or more forms that have the same number and kind of atoms and the same atomic arrangement, but differ in their spatial relationship. In the case of an asymmetric internucleoside phosphorus atom, there are two possible stereoisomeric configurations.

By the term "stereoisomerically pure" or "stereochemically pure" is meant that one stereoisomer is present in the substantial absence of other stereoisomer. When referring to a molecule containing at least one asymmetric internucleoside phosphorus atom, the terms mean that one stereoisomeric configuration of the asymmetric internucleoside phosphorus atom is present in the substantial absence of the other stereoisomeric configuration. The term "stereochemically pure" as used herein preferably means that at least about 70% by weight, more preferably at least about 80% by weight, and most preferably at least about 90% by weight, of a dimer or oligonucleotide of a particular stereoisomeric configuration is present to the exclusion of the other stereoisomeric configuration. "Resolution" of stereoisomers indicates a means by which the stereoisomers may be separated from each other to yield stereochemically pure isomers. A "point racemic mixture" or "point racemate" is defined herein to be a mixture of stereoisomers in which both stereoisomers at a particular asymmetric phosphorus atom are present. Such a "point racemic mixture" will typically, although not necessarily, contain on the order of 40% to 60% of one stereoisomer and, correspondingly, 60% to 40% of the other stereoisomer, although, generally, the two stereoisomers will be present in approximately equal quantities. For example, in a dimer having an asymmetric internucleoside phosphorus, or in an oligonucleotide having one such asymmetric phosphorus, a point racemic mixture will have generally contain approximately equal amounts of each stereoisomer.

The term "stereouniform" when referring to a particular cationic internucleoside linkage having an asymmetric phosphorus atom such that the internucleoside linkage is capable of existing in one of two distinct stereoisomeric configurations intends that a substantial portion of such molecules containing the internucleoside linkage have the linkage present in a distinct stereoisomeric configuration. Preferably, a "substantial portion" intends that greater than 70%, more preferably greater than 80% and most preferably greater than 90% of such internucleoside linkages are present in a stereoisomeric configuration.

Stereoisomers may be resolved by any of a variety of methods known in the art. For example, some racemic mixtures crystallize in such a manner that molecules of like stereoisomeric configuration assemble into visibly asymmetric crystals. Such crystals may be physically separated to yield stereochemically pure stereoisomers.

A second method that is well known in the art involves a chemical procedure by which a racemic mixture is allowed to react with a second, standard asymmetric molecule, e.g., if the racemate is an acid an optically active amine such as quinine, brucine or strychnine may be used to resolve the mixture. This method creates two stereoisomers that may be separated by standard physical means, e.g., distillation, crystallization, chromatography and the like.

In the case of oligonucleotides containing substituents attached to the internucleoside phosphorus, the isomers determined by chirality at the internucleoside phosphorus are actually diastereomers, since the sugar components of the oligonucleotide backbone are chiral; diastereomers can be separated by conventional methods such as distillation, crystallization, chromatography or the like.

Stereoisomers which are diastereomers may be separated using thin layer chromatography ("TLC") or column chromatography using an achiral medium. TLC resolution of the stereoisomers may be done on an appropriate TLC plate containing a solid phase, e.g., silica, which optionally contain chiral reagents, or the like and which are effective to resolve stereoisomers. The stereoisomers separated by TLC may be characterized by their differential solubility in the TLC substrate and a solvent used to develop the plate. Typically, the differential solubility is expressed by determining the migration of the compound on the plate in a particular solvent system relative to the migration of the solvent system used to develop the plate. Thus, the location of the stereoisomers on the plate after development thereof is expressed as the distance moved from the spot where the compound is applied relative to the location of the solvent front; this ratio is typically referred to as the $R_f$ of the stereoisomer. Column chromatographic resolution of the stereoisomers may also be done using a solid phase matrix, e.g., silica gel, which optionally contains chiral reagents using techniques and reagents that are well known in the art. The stereoisomer having the higher $R_f$, i.e., higher mobility on a TLC plate in a particular solvent system, or eluting first from the column is designated herein the "first-eluting" isomer while the stereoisomer having the lower $R_f$ or eluting second from the column is designated herein the "second-eluting" isomer.

The absolute stereochemistry at phosphorus atoms can be determined by the 2D-NMR method of Loschner et al. (1990) *Nucleic Acids Res.* 18:5083–5088 as described by Fathi et al. (1994), *Nucleic Acids Res.*, supra. The absolute stereochemical configuration may also be determined by conventional methods well known in the art such as by optical rotatory dispersion or circular dichroism measurements.

"Optional" or "optionally" means that the subsequently described event or circumstance may or may not occur, and that the description includes instances where said event or circumstance occurs and instances where it does not. For example, the phrase "optionally substituted alkylene" means that an alkylene moiety may or may not be substituted and that the description includes both unsubstituted alkylene and alkylene where there is substitution.

The Novel Oligonucleotides

The novel oligonucleotides of this invention contain cationic internucleoside linkages having the structure (I)

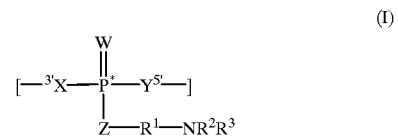

with W, X, Y, Z, $R^1$, $R^2$ and $R^3$ as defined above for structure (I).

In the structure, P* represents an asymmetric phosphorus atom present in, for example, a phosphotriester, a phosphoramidate, a phosphothioester or an alkylaminophosphonate linkage. The oligonucleotide may contain any combination of anionic and/or cationic internucleoside linkages. In an oligonucleotide, the cationic internucleoside linkages may be any combination of phosphotriester, phosphoramidate, phosphothioester, alkylaminophosphonate linkages.

As a result of the presence of an asymmetric phosphorus atom, the cationic internucleoside linkages are capable of existing in one of two stereoisomeric configurations. The oligonucleotide may be prepared as described and exemplified below such that only one of the two stereoisomers is present at any predetermined internucleoside linkage, i.e., such that a predetermined internucleoside linkage in an oligonucleotide is stereouniform.

As noted above, W may be O, S and Se. In a particularly preferred embodiment, wherein P* is an asymmetric phosphorus atom and each such linkage is stereouniform, W is S.

X and Y may be independently O, S, C($R^4$)$R^5$ where $R^4$ and $R^5$ are independently selected from the group consisting of H and $C_1$–$C_6$ alkyl, and $NR^6$ where $R^6$ is H or $C_1$–$C_6$ alkyl. Preferably, X and Y are independently O, S CH$_2$ or NH, more preferably X and Y are both O.

Z can be O, S, $C_1$–$C_6$ alkylene, $C_2$–$C_6$ alkenylene, $C_2$–$C_6$ alkynylene and $NR^7$ where $R^7$ is H or $C_1$–$C_6$ alkyl. When P* is an asymmetric phosphorus atom and each cationic internucleoside linkage is stereouniform Z is O, S or $NR^7$ when W, X and Y are O. In a preferred stereouniform cationic internucleoside linkage, Z is O or NH.

In other preferred embodiments of the invention, the cationic internucleoside linkages are not necessarily stereouniform. In these embodiments, when W, X and Y are O, Z is O or S. In one set of these embodiments, the oligonucleotide contains alternating cationic and anionic internucleoside linkages.

$R^1$ is selected from the group consisting of lower alkylene, lower alkenylene, lower alkynylene, monocyclic arylene and a bond. Thus, for example, when $R^1$ is a bond, Z is linked directly to $NR^2R^3$. $R^1$ is selected to provide an spacer between the internucleoside phosphorus and the cationic center and may be chosen to optimize the affinity of the oligonucleotide containing cationic internucleoside linkages for hybridizing with nucleic acids. Particularly preferred groups useful as $R^1$ include (CH$_2$)$_2$ or (CH$_2$)$_3$.

$R^2$ and $R^3$ may be any combination of H, lower alkyl, lower alkyl substituted with 1 to 4 $NH_2$ groups, and monocyclic aryl. Alternatively, or $R^2$ and $R^3$ may be linked to form a five- or six-membered alkyl or aryl ring or an N-, O- or S-containing heterocycle. It is preferred that, when P* is an asymmetric phosphorus atom and each such linkage is stereouniform, $R^2$ and $R^3$ are H, $CH_3$ or lower alkyl terminally substituted with 1 $NH_2$ group. More preferably, $R^2$ and $R^3$ are $CH_2NH_2$ or $CH_2CH_2NH_2$. Preferred heterocycles include pyrrole, pyrrolidine, pyridine, piperidine, morpholine, quinoline, indole, pyrimidine, piperazine, pipecoline, imidazole, benzimidazole and purine, which may be unsubstituted or substituted with halogen or $C_1$–$C_6$ alkyl. Preferred heterocycles include imidazole, morpholine, pyrrolidine, piperazine pipecoline, methylpiperazine.

Generally, W, X, Y, Z, $R^1$, $R^2$ and $R^3$ are chosen to provide an oligonucleotide with cationic oligonucleoside linkages that are chemically insensitive to hydrolysis under physiological condition, that provide an oligonucleotide that is resistant to nucleases and/or that form stable duplexes with complementary oligonucleotides.

In one particularly preferred embodiment, the cationic internucleoside linkage has the structure (III)

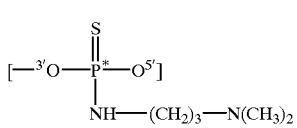

(III)

wherein P* represents an asymmetric phosphorus atom, such that the linkage exists in stereoisomeric configuration that corresponds to the configuration of the first-eluted stereoisomer when a point racemic mixture of a nucleotide dimer containing the internucleoside linkage is resolved using silica gel column chromatography.

The oligonucleotide disclosed and claimed herein may have any proportion of anionic PDE linkages replaced by cationic internucleoside linkages. Thus, the oligonucleotide may contain as few as about one of the anionic PDE linkage replaced by a cationic internucleoside linkage and may have as many as 100% of the anionic PDE linkages replaced with cationic linkages. The proportion of negative and positive charges can be varied to yield an oligonucleotide having a desired net charge; the oligonucleotide may have an overall positive, neutral or negative charge depending on the number of cationic internucleoside linkages incorporated therein.

The oligonucleotide may be prepared to contain alternating anionic and cationic internucleoside linkages. As described hereinbelow in Example 4, oligonucleotides containing alternating anionic and cationic internucleoside linkages form more stable duplex with DNA or RNA than the anionic counterpart.

The anionic and cationic internucleoside linkages may be randomly distributed throughout the oligonucleotide or may be present in the oligonucleotide in blocks of anionic linkages and cationic linkages.

In one preferred embodiment of the invention, the oligonucleotide has a stereouniform cationic internucleoside linkage between selected nucleosides in the oligonucleotide.

Oligonucleotides having cationic internucleoside linkages may be prepared using conventional oligonucleotide synthetic techniques. For example, an oligonucleotide containing a cationic internucleoside linkage having a predetermined stereoisomeric configuration at that linkage can be prepared by synthesizing dimer blocks having the desired phosphotriester, phosphoramidate or alkylaminophosphonate linkage, resolving the stereoisomers of the dimer block and incorporating the resolved stereoisomer of the dimer block into an oligonucleotide using solid phase oligonucleotide synthetic techniques. Either the first- or second-eluting stereoisomer may be incorporated into an oligonucleotide. For example, the cationic thymidylate dimer having the two stereoisomeric structures (IVa) and (IVb)

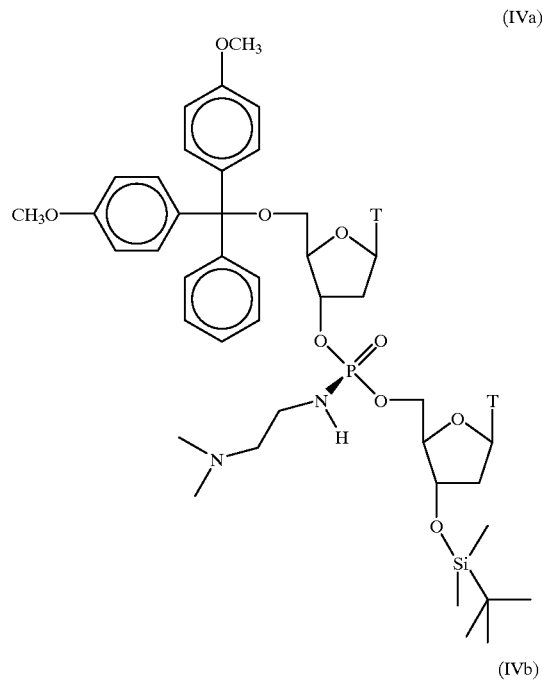

(IVa)

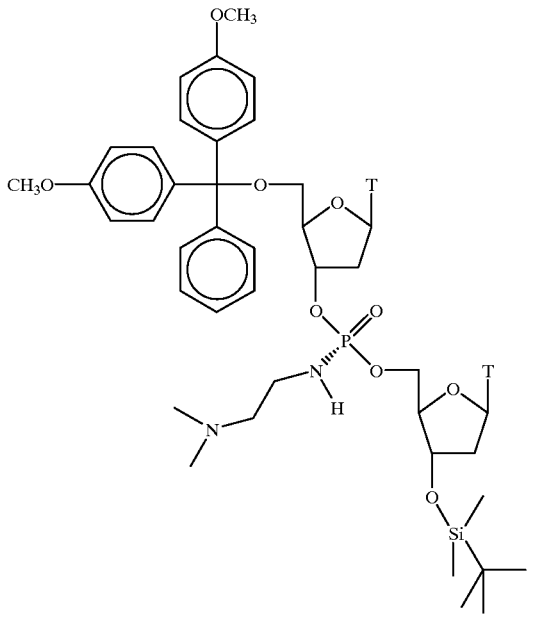

(IVb)

where T represents a thymidylate nucleoside, can be prepared by reacting 5'—HO—T—O—t-butyldimethyldisilyl ("TBDMS") with dimethoxytrityl ("DMT")—T—O—P(OCH_3)—N(iPr)_2 as described in Example 1 and depicted in Scheme 1.

Scheme 1
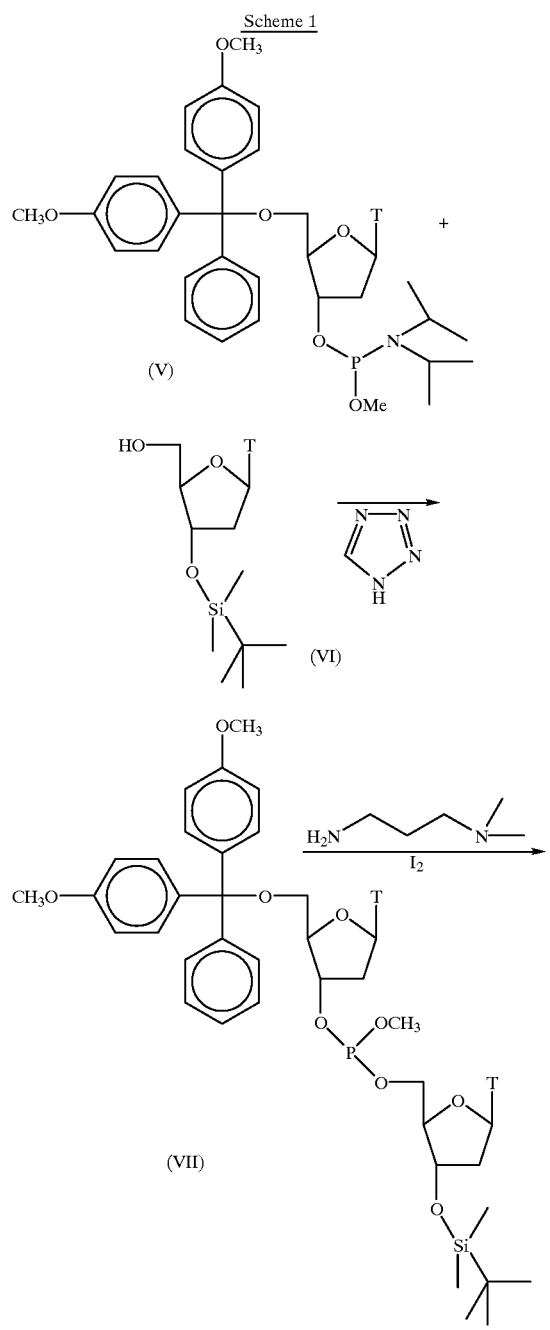
(V)
(VI)
(VII)
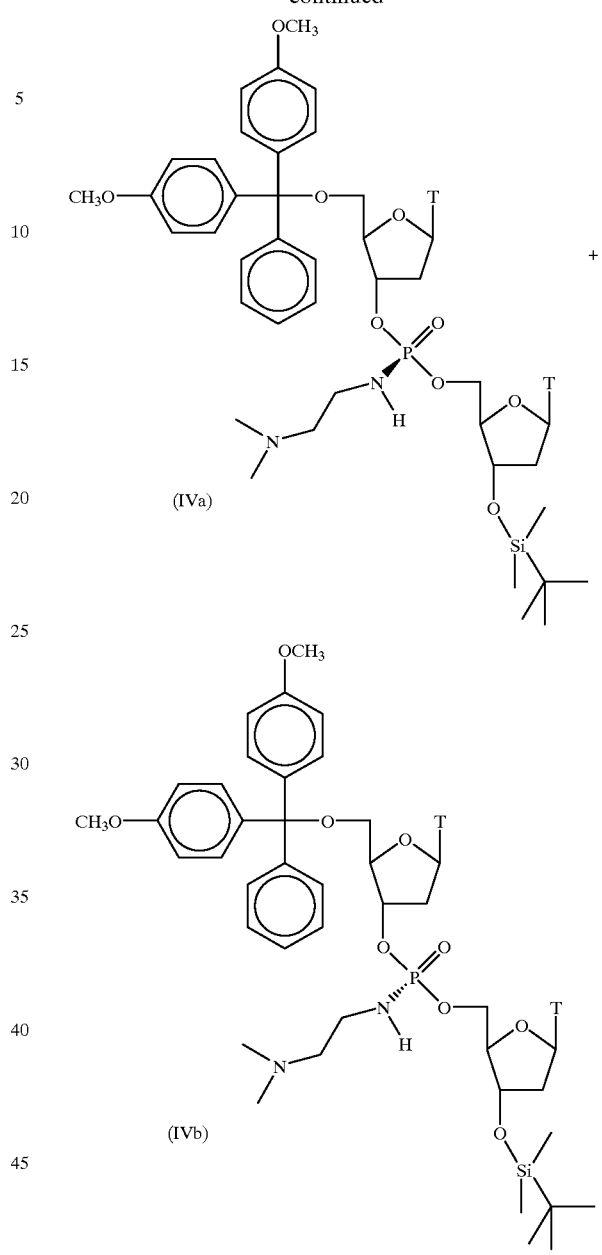
(IVa)
(IVb)
DMT—T—O—P(OCH$_3$)—N(CHCH$_3$)$_2$) (V) was reacted with 5'-HO—T—O—TBDMS (VI) in tetrazole. After the reaction was essentially complete, the reaction mixture was concentrated, diluted with $CH_2Cl_2$ and extracted with $NaHCO_3$ and 80%-saturated NaCl. The organic phase was dried, filtered and evaporated to yield the crude phosphite-triester intermediate (VII). The intermediate was reacted with 3-diaminopropylamine in the presence of iodine. The product of the final reaction is a point racemic mixture of crude DMT—T—O—P(O)—(NH—($CH_2$)—N($CH_3$)$_2$)—O—T—O—TBDMS (IVa and IVb).

In addition, the point racemate may be used to prepare an oligonucleotide having a cationic internucleoside linkage where the configuration of the linkage does not need be stereospecific.

Oligomers having cationic phosphoramidate internucleoside linkages using the two-step method described in Example 6. The reaction involves oxidation of a pre-synthesized dimer having a methyl phosphite-triester linkage with dithiodipyridine to give an activated S-Pyr-phosphorothiodiester. The newly formed stereoisomers may be resolved and the S-Pyr group thereafter displaced with reaction amine such as 3-dimethylpropylamine to yield a dimer having the desired phosphoramidate diester linkage in the desired stereochemical configuration.

The two-step method described above and in Example 6 may be used for solid phase synthesis of cationic phosphoramidate-linked oligomers. During chain elongation, the oligomer is not exposed to amine solutions and at the conclusion of the reaction all S-Pyr-phosphorothiodiester linkages are converted to phosphoramidate linkages. This method of modifying internucleoside linkages during solid phase synthesis does not result in stereospecificity at the phosphoramidate linkages.

Other methods by which oligonucleotides containing cationic internucleoside linkages will be apparent to those skilled in the art.

Oligonucleotides having cationic internucleoside linkages find utility as probes for nucleic acids as a result of the increased stability of duplexes formed therewith. Cationic and zwitterionic oligonucleotides offer the possibility of using salt and/or pH to further control duplex formation involving nucleic acid targets. Typically, hybridization of oligonucleotides with RNA targets can be difficult because of extensive secondary and tertiary structures in the RNA; however, at low salt concentrations these structures are much less stable. Hybridization of RNA targets with cationic oligonucleotides which may be controlled by salt concentration, i.e., which form stable duplexes at low salt, allows stable duplex formation.

For example, oligonucleotides having increased duplex stability will find utility in nucleic acid hybridization assays commonly used in genetic research, biomedical research and clinical diagnostics. In a basic nucleic acid hybridization assay, single-stranded analyte nucleic acid is hybridized to a labeled single-stranded nucleic acid probe and resulting labeled duplexes are detected. Hybridization steps in such assays are performed under appropriate stringency conditions. Stringency can be controlled by altering a parameter which is a thermodynamic variable. Such variables are well known in the art, and include formamide concentration, salt concentration, chaotropic salt concentration, pH, organic solvent content, and temperature. Preferred stringency controls are pH and salt concentration. The stringency will be varied depending on the length and nature of the analyte sequence.

Variations of this basic scheme have been developed to enhance accuracy, facilitate the separation of the duplexes to be detected from extraneous materials, and/or amplify the signal that is detected. One such assay is described in detail in commonly assigned U.S. Pat. No. 4,868,105 to Urdea et al., the disclosure of which is incorporated herein by reference. In addition, the ability to control duplex formation by varying salt concentration and/or pH makes oligonucleotides having cationic internucleoside linkages particular useful in nucleic acid hybridization assays for decreasing background noise due to nonspecific hybridization as described in commonly assigned U.S. patent application Ser. No. 08/298,073 to Collins et al., the disclosure of which is incorporated herein by reference.

Another application in which the construction of hybridizing oligonucleotides containing cationic internucleoside linkages finds utility is in the design of antisense compounds. Antisense compounds, as explained, for example, in Ching et al. (1989) *Proc. Natl. Acad. Sci. U.S.A.* 86:10006–10010, Broder et al. (1990) *Ann. Int. Med.* 113:604–618, Loreau et al. (1990) *FEBS Letters* 274:53–56, and PCT Publication Nos. WO91/11535, WO91/09865, WO91/04753, WO90/13641, WO91/13080 and, WO 91/06629, are oligonucleotides that bind to and disable or prevent the production of the mRNA responsible for generating a particular protein. Conventional antisense molecules are generally capable of reacting with a variety of oligonucleotide species. A triplex structure, e.g., an antisense molecule hybridized to a double-stranded oligonucleotide target, can also provide an antisense function.

The oligonucleotides of the invention have properties that make them more desirable than the naturally linked oligonucleotides as antisense molecules. Oligonucleotides having cationic internucleoside linkages are more resistant to nucleases which hydrolyze naturally occurring oligonucleotide; therefore, oligonucleotides having cationic internucleoside linkages have a longer half-life in cells. Such oligonucleotides can interact with complementary oligonucleotides in the cells with greater stability than naturally occurring counterparts. The formation of this substantially stable complex within the cell by an oligonucleotide having a cationic internucleoside linkage allows the selective inhibition of gene expression.

Experimental

The practice of the present invention will employ, unless otherwise indicated, conventional techniques of synthetic organic chemistry, biochemistry, molecular biology, and the like, which are within the skill of the art. Such techniques are explained fully in the literature. See, e.g., Sambrook, Fritsch & Maniatis, *Molecular Cloning: A Laboratory Manual*, Second Edition (1989); *Oligonucleotide Synthesis* (M. J. Gait, ed., 1984); Nucleic Acid Hybridization (B. D. Hames & S. J. Higgins, eds., 1984); and the series, *Methods in Enzymology* (Academic Press, Inc.).

All patents, patent applications, and publications mentioned herein, both supra and infra, are hereby incorporated by reference.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g., amounts, temperature, etc.) but some experimental error and deviation should be accounted for. Temperature is always given in degrees C and, unless otherwise indicated, pressure is at or near atmospheric.

NMR Spectroscopy. In the following Examples, NMR spectra were recorded on a Varian 300 MHz instrument. $^{31}$P spectra were run at 121 MHz with reference to trimethylphosphite set at 140 ppm.

High Performance Liquid Chromatography. Reverse phase high performance liquid chromatography ("RP-HPLC") analysis and purification were performed on a Supelco LC-18 column 5 micron (25 cm×4.6 mm) eluted with a 0–50% gradient over 25 minutes of $CH_3CN$ into 5% $CH_3CN$ in 0.1 M triethylammonium acetate buffer, pH 7.5, flow rate 1 mL/min.

EXAMPLE 1

Synthesis of Cationic Dimer

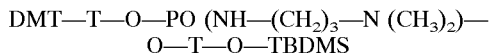

5'—HO—T—O—TBDMS (VI) (3.7 grams; 10.4 mmole) and tetrazole (20 mmole) were coevaporated with dry acetonitrile (2×100 mL) and the residue was dissolved in dry acetonitrile (50 mL). DMT—T—O—P(OCH$_3$)—N(iPr)$_2$ (V) (10 mmole) was dissolved in dry acetonitrile (50 mL) in a separate round bottom flask and then slowly added to the 5'—HO—T—O—TBDMS/tetrazole solution over a five minute period of time. Thin layer chromatography analysis on silica plates developed twice in 5% methanol/CH$_2$Cl$_2$, where the DMT-positive product migrated slightly faster than 5'—HO—T—O—TBDMS, indicated that the reaction appeared to be complete in less than 5 minutes.

The reaction mixture was gently concentrated to a small volume, diluted with 400 mL CH$_2$Cl$_2$ and the organic phase extracted with 5% aqueous NaHCO$_3$ (400 mL) and 80%-saturated aqueous NaCl (400 mL). The organic phase was dried over solid NaSO$_4$, filtered and evaporated to dryness. The residue was coevaporated with toluene (100 mL) and acetonitrile (2×200 mL) to give 10 grams of a crude phosphite-triester intermediate (VII).

The crude intermediate, which was used directly without further purification, was dissolved in acetonitrile (200 mL). Undiluted 3-diaminopropylamine (10 mL; 16 mmole) was added directly to the solution followed by the drop-wise addition of a solution of iodine (2.53 grams; 10 mmole) in acetonitrile (100 mL) with rapid stirring. The violet color of iodine faded immediately on addition and a slightly yellow color persisted after addition concluded. The reaction mixture was left at 4° C. for 18 hours.

The reaction mixture was then gently concentrated to a small volume and diluted with 400 mL CH$_2$Cl$_2$. The organic phase of this preparation was extracted with 15% sodium bisulfite (300 mL), 5% aqueous NaHCO$_3$ (2×400 mL) and 80% saturated aqueous NaCl (2×400 mL). The organic phase was dried over solid NaSO$_4$, filtered and evaporated to dryness. The residue was coevaporated with toluene (100 mL) and acetonitrile (2×200 mL) to give 12 grams of crude DMT—T—O—PO(NH—(CH$_2$)$_3$—N(CH$_3$)$_2$)—O—T—O—TBDMS ((IVa) and (IVb)).

The product was fractionated by silica gel chromatography ("600 mL" Merck silica gel 60 poured in a solvent system of 2% triethylamine ("TEA")/CH$_2$Cl$_2$) using a gradient of methanol (0–6%) in 2% TEA/CH$_2$Cl$_2$ taking 100 mL fractions. Fractions 16–25 were pooled and concentrated. The fractionation was repeated by silica gel chromatography as described above with a drawn-out gradient of methanol (2% (8 fractions), 4% (16 fractions), 5% (16 fractions) and 6% (16 fractions) methanol) in 2% TEA/CH$_2$Cl$_2$ taking 50 mL fractions. Three pools were isolated: #1, fractions 19–22; #2, fractions 23–32; and #3, fractions 33–40. Each pool was concentrated and coevaporated with toluene and acetonitrile to yield three pools with the following characteristics:

| Pool | Weight (gm) | Amount (mmole) | NMR (purity)[1] | TLC[2] |
|---|---|---|---|---|
| 1 | 1.17 | 0.95 | 8.85 ppm (100%) | faster 100% |
| 2 | 4.17 | 3.5 | 9.05/8.85 (60:40) | faster/slower 60:40 |
| 3 | 0.82 | 0.7 | 9.1/8.9 (95:5) | faster/slower 95:5 |

[1] $^{31}$P NMR experiments were performed with a approximately 0.05 M solution of the respective dimer pool in acetonitrile using d$_6$-DMSO as external standard; Varian 300.
[2] TLC: Merck silica 60F plates on alumina; pre-developed in 8% MeOH/2% TEA/CH$_2$Cl$_2$ followed by applying about 0.05 M sample and developing in the same solvent system; the first-eluting fraction had an R$_f$ of 0.62 while the second-eluting had an R$_f$ of 0.40.

Pool #2 from the initial purification of DMT—T—O—PO(NH—(CH$_2$)$_3$—N(CH$_3$)2)—O—T—O—TBDMS was further fractionated by silica gel chromatography ("400 mL" Merck silica gel 60 poured in a solvent system of 2% TEA/CH$_2$Cl$_2$) with a gradient of methanol (2% (16 50-mL fractions), 3% (8×50 mL, 10×25 mL), 4% (16×50 mL) and 5% (6×50 mL)) in 2% TEA/CH$_2$Cl$_2$. Three pools were isolated as follows. Pool #1, fractions 24–34: first-eluting isomer, 1.62 grams; Pool #2, fractions 23–32: mixture of isomers, 0.73 gram; and Pool #3, fractions 33–40: second-eluting isomer, 1.2 grams.

Removal of the TBDMS group was achieved with tetrabutylammonium fluoride ("TBAF"). Silica purified DMT—T—O—PO(NH—(CH$_2$)$_3$—N(CH$_3$)2)—O—T—O—TBDMS, Pool #1 from the initial purification (1.14 grams; 0.95 mmole), in 19 mL acetonitrile was treated with 5 equivalents of TBAF (5 mL of 1 M of TBAF in THF) for 2.5 hours at which time the reaction was more than virtually complete. The reaction mixture was diluted with 250 mL methylene chloride and extracted with 5% aqueous NaHCO$_3$ (250 mL) and 80%-saturated aqueous NaCl (250 mL). The organic phase was dried over solid NaSO$_4$, filtered and evaporated to dryness. The residue was coevaporated with toluene (100 mL) and acetonitrile (2×200 mL). Crude DMT—T—O—PO(NH—(CH$_2$)—N(CH$_2$)$_2$)—O—T—OH from Pool #1 was purified by silica gel chromatography ("250 mL" Merck silica gel 60 poured in a solvent system of 2% TEA/CH$_2$Cl$_2$ using a gradient of methanol (0–18%) in 2% TEA/CH$_2$Cl$_2$ (0% (4 fractions), 3% (4 fractions), 6% (8 fractions), 9% (8 fractions), 12% (8 fractions), 15% (8 fractions), 18% (8 fractions)) in 2% TEA/CH$_2$Cl$_2$ taking 50 mL fractions. Fractions 32–40 were pooled.

Concentration of the pooled fractions 32–40 yielded pure DMT—T—O—PO(NH—(CH$_2$)$_3$—N(CH$_3$)$_2$)—O—T—OH (first-eluting isomer; 0.61 gram; 0.57 mmole). $_{31}$P MNR in CH$_2$Cl$_2$ with d$_6$—DMSO as external standard: 8.3 ppm (100%); $^{31}$P MNR in CH$_3$CN with d$_6$—DMSO as external standard: 8.87 ppm (100%).

Similarly, silica-purified DMT—T—O—PO(NH—(CH$_2$)$_3$—N(CH$_3$)$_2$)—O—T—O—TBDMS, Pool #3 from initial purification (0.8 gram; 0.7 mmole), was treated with 5 equivalents of TBAF. Workup and purification, as described above for DMT—T—O—PO(NH—(CH$_2$)$_3$—N(CH$_3$)2)—O—T—O—TBDMS, Pool #1, yielded pure DMT—T—O—PO(NH—(CH$_2$)$_3$—N(CH$_3$)$_2$)—O—T—OH (slower isomer; 0.57 gram; 0.53 mmole). $^{31}$P NMR (CH$_2$Cl$_2$ with d$_6$—DMSO as external standard): 8.57 ppm (98%).

EXAMPLE 2

Synthesis of DMT—T—O—PO (NH—(CH$_2$)$_3$—N(CH$_3$)$_2$)—O—T—O—P(N(iPr)$_2$)—O—BCE DMT—T—O—PO(NH—(CH$_2$)$_3$—N(CH$_3$)$_2$)—O—T—OH (first-eluting isomer; 0.61 gram; 0.57 mmole) in CH$_2$Cl$_2$ containing DIPEA (5.7 mmole) was reacted with Cl—P(N(iPr)$_2$)—O—BCE (1.14 mmole; two-fold excess), wherein BCE is β-cyanoethyl. The progress of the reaction was monitored by TLC in 8% methanol in 2% TEA/CH$_2$Cl$_2$). The reaction mixture was left at 4° C. for 18 hours. The reaction mixture was diluted with 250 mL methylene chloride and extracted with 5% aqueous NaHCO$_3$ (250 mL) and 80% saturated aqueous NaCl (250 mL). The organic phase was dried over solid NaSO$_4$, filtered and evaporated to dryness. The residue was coevaporated with toluene (50 mL) and acetonitrile (2×100 mL) to give 0.6 grams (0.47 mmole). $^{31}$P NMR (CH$_3$CN with d$_6$—DMSO as external standard): 148.5, 148.3, 8.87 ppm (integration: 1/1 phosphoramidite to phosphoramidate).

DMT—T—O—PO(NH—(CH$_2$)$_3$—N(CH$_3$)$_2$)—O—T—OH (second-eluting isomer; 0.57 gram; 0.53 mmole) was converted to the BCE phosphoramidite using the same procedure to give 0.6 grams product. $^{31}$P NMR (CH$_3$CN with d$_6$—DMSO as external standard): 148.5, 148.3, 9.07 ppm (integration: 1/1 phosphoramidite to phosphoramidate).

The stereoisomers of DMT—T—O—PO(NH—(CH$_2$)$_3$—N(CH$_3$)$_2$)—O—T—O—TBDMS were readily separated by TLC and column chromatography on silica, but after removal of the 3'—O—TBDMS group it was not possible to resolve them by TLC in any solvent system.

NMR data for DMT—T—O—PO(NH—(CH$_2$)$_3$—N(CH$_3$)2)—O—T—O—P(N(iPr)$_2$)—(O—BCE).

(a) first-eluting isomer. $^1$H NMR (CDCl$_3$) δ (ppm): 9.0 (s, 1H, NH, exchangeable by D); 7.48 (s, 1H, H6); 7.45 (s, 1H, H6); 7.45–6.8 (m, 13H, trityl); 6.16 (t, 1H, H1'); 6.15 (t, 1H, H1'); 5.05 (m, 1H, H3'); 4.16 (m, 1H, H3'); 4.1 (m, 1H, H4'); 4.05–3.9 (m, 2H, H5', 5'); 3.85 (m, 1H, H4'); 3.75 (s, 6H, OCH3); 3.28–3.21 (m, 2H, H5'); 2.9–2.7 (m, 4H, NCH2); 2.46 (m, 2H, H2'); 2.3 (s, 6H); 2.06 (m, 2H, H2'); 1.74 (s, 3H, CH3); 1.7–1.5 (m, 2H, CH2); 1.43 (s, 3H, CH3); 1.0 (s, 9H); 0.0 (s, 6H); $^{31}$P NMR (CDCl$_3$): 8.75 ppm.

(b) second-eluting isomer: $^{31}$P NMR (CDCl$_3$): 9.1 ppm. NMR data for DMT—T—O—PO(NH—(CH$_2$)$_3$—N(CH$_3$)$_2$)—O—T-3'—O—P(N(iPr)$_2$)—O—BCE.

(a) First-eluting isomer: $^{31}$p NMR 148.5 ppm, 147.9 ppm, 8.75 ppm (integration ratio of phosphoramidite/phosphoramidate=1:1).

(b) Second-eluting: 148.45 ppm, 147.96 ppm, 9.1 ppm (integration ratio of phosphoramidite/phosphoramidate=1:1).

EXAMPLE 3

Synthesis of 5'O—DMT—U(2'—O—(CH$_3$))-3'O—P(O) (NH—(CH$_2$)$_3$—N(CH$_3$)$_2$)-5'—O—U(2'—O—(CH$_3$))-3'—OR 5'—O—DMT—U(2'—O—CH$_3$)-3'—O—P(O)(NH—(CH$_2$)$_3$—N(CH$_3$)$_2$)-5'—O—U(2'—O—CH$_3$)-3'—OR, wherein R is TBDMS, H or P(O—CH$_2$CH$_2$CN)—N(iPr)$_2$ was synthesized as follows.

5'—O—DMT—U(2'—O—CH$_3$)-3'—O—P(O—CH$_3$)—N(iPr)$_2$ (MW 721) 7.9 mmole, was prepared from commercially available 5'—O—DMT—U(2'—O—CH$_3$)-3'—OH, purchased from ChemGenes (Waltham, MA). 5'—O—U(2'—O—CH$_3$)-3'—O—TBDMS was prepared from 5'—O—DMT—U(2'—O—CH$_3$)-3'—OH purchased from Monomer Sciences (Huntsville, Ala.). The fully protected derivative was prepared by first coupling 5'—O—DMT—U(2'—O—CH$_3$)-3'—O—P(O—CH$_3$)—N(iPr)$_2$ (MW 7210) (7.9 mmole) and 5'—O—U(2'—O—CH$_3$)-3'—O—TBDMS (8 mmoles) in the presence of tetrazole (16 mmoles) to give the phosphitetriester intermediate. The phosphitetriester intermediate (VII), used directly after aqueous workup essentially as described in Example 1, was mixed with a two-fold excess of 3-dimethylaminopropylamine and reacted with 80 mL of 0.1 M solution of iodine in CH$_3$CN. After aqueous workup as described in Example 1, this reaction yielded 8.54 grams of crude product. $^{31}$P-NMR (in CH$_3$CN with d$_6$—DMSO as external reference): 8.9 and 9.5 ppm.

Purification by silica gel chromatography ("700 mL" Merck silica gel 60) performed as described in Examples 1 and 2 yielded two fraction pools: the first-eluting pools (fraction nos. 32–44, 1.69 grams, $^{31}$P-NMR 8.9 ppm (100%)) and fraction nos. 47–60, SLOWER, 1.62 grams, $^{31}$P-NMR 8.9 ppm (>5%), 9.5 ppm (80%), 10.2+10.7 ppm (total 18%) (unknown identity).

EXAMPLE 4

Preparation of Cationic Oligomers with Alternating Stereo-defined Phosphoramidate Linkages Oligonucleotides having alternating anionic and stereo-uniform cationic phosphoramidate linkages were prepared by incorporating cationic stereoisomerically pure Tp(+)T dimer phosphoramidites, wherein Tp(+)T indicates a cationic dimethylaminopropylamido substituent on the internucleoside phosphorus atom and Tp(–)T indicates a conventional phosphodiester internucleoside linkage.

The following oligomers were synthesized using the methods described in Examples 1–3: (Tp(+)Tp)$_7$T (using the first-eluting isomer); (Tp(+)Tp)$_7$T (using the second-eluting isomer); and (Tp(+)Tp)$_7$T (point racemate, i.e., a random mixture of first- and second-eluting isomers at any one position).

Oligomer syntheses using cationic dimers were performed on a Millipore Expedite DNA synthesizer using a 10 minutes coupling step. DMT—Tp(+)T BCE (first-eluting isomer or second-eluting isomer, or a point racemate (approximately equal amounts of first- and second-eluting isomers)) was dissolved in dry acetonitrile to a concentration of 0.1 M. The oligomer sequence synthesized was DMT-(Tp(+)Tp)$_7$T by seven cycles of dimer addition; the final DMT was not removed. The crude oligomer was cleaved from the support with aqueous NH$_4$OH (1 hour/20° C.). The supernatant was concentrated and the residue was redissolved in 400 μL water. Analysis of the crude oligomer product by high performance liquid chromatography ("HPLC") done as described in the Experimental section in all cases showed one major peak eluting around 20 minutes.

The full-length DMT product was purified by reverse phase-HPLC ("RP-HPLC") by injecting 100 μL (about 43 A$_{260}$ units). The peak eluting at around 20 minutes was collected (about 1 mL) and evaporated to dryness. The residue was redissolved in 200 μL 80% aqueous acetic acid for 1 hour to remove the 5'-terminal DMT group. The acid solution was removed by evaporation and the residue redissolved in 100 μL 80% aqueous acetic acid. The solution was allowed to stand for 1 hr at room temperature and was then evaporated to dryness. The residue was dissolved in about 0.5 mL water. The aqueous solution was washed twice with about 0.5 mL ethyl acetate and then lyophilized. Fine particular matter was removed by centrifugation. The detritylated oligomer was finally purified by RP-HPLC using the same procedure as described above.

EXAMPLE 5

Preparation of Dimer Blocks with Isomer Resolution

The methods described in this Example can be used to synthesize cationic oligomers from monomer units on a solid support using one monomer type. This method was exemplified using nucleoside methyl phosphoramidites.

A. The phosphorothioate dimer Tp(S)T was treated with 2–4-fold excess $MeSO_2$-Cl in pyridine. The starting material was completely consumed to yield two new $^{31}$P NMR signals at 67/68 ppm. When the reaction mixture was quenched with dimethylaminopropylamine ("DMAPA") the 67/68 ppm signals were immediately replaced with a new pair at 72/73 ppm; no signals corresponding to Nu—O—P-(O)(NH-R)—O—Nu at 8.8/9.4 ppm were observed.

B. $MeSO_2$-Cl (20 μL; 2-fold excess) was added to 5'—O—DMT—T—O—P(S)O—O—5'-T-3'—O—TBDMS in pyridine (0.6 mL of a 0.2 M solution) at 20° C. The reaction was complete in minutes as judged by $^{31}$P NMR with two new signals at 67/6 and 67/0 ppm. DMAPA was added (4-fold excess over the phosphorothioate and the reaction was allowed to proceed. After less than 5 minutes $^{31}$P NMR showed that the two signals at 67.6 and 67.0 ppm had completely disappeared and were replaced by two new signals at 73.5 and 72.9 ppm. The reaction mixture was diluted with ethyl acetate, extracted with $NaHCO_3$ and NaCl. TLC of the crude product showed two DMT/sugar positive spots which migrated slightly faster than 5'—O—DMT—T—O—P(O) (NH—$(CH_2)_3$—$N(CH_3)_2$)—O—5'—T-3'—O—TBDMS in 2% TEA/8% MeOH/90% $CH_2Cl_2$. Thus, the reaction leads exclusively to O-activation without any S-activation.

EXAMPLE 6

Preparation of Cationic Dimers Having a Cationic Internucleoside Phosphoramidate Linkage This example describes a two-step synthesis of cationic phosphoramidate linked oligomers. The reaction involves oxidation of a methyl phosphite-triester linkage with dithiodipyridine to give an activated S-Pyr-phosphorothiodiester followed by displacement with amine to yield the desired phosphoramidate diester linkage. This scheme is attractive for solid phase synthesis of cationic phosphoramidate-linked oligomers. During chain elongation, the oligomer is not exposed to amine solutions and at the conclusion of the reaction all S-Pyr-phosphorothiodiester linkages are converted to phosphoramidate linkages.

Triethylamine (0.1 mL) was added to a solution of DMT—$O^{5'}$—T—$O^{3'}$—P(O—($CH_3$))—$O^{5'}$—$O^{3'}$—TBDMS in $CH_3CN$ (0.3 mL; 0.2 M). A five-fold excess of dithiopyridine in $CH_3CN$ (0.3 mL; 1.0 M) was added and the reaction was allowed to proceed at 20° C. The progress of the reaction was followed by NMR.

The initial two signals at 140 ppm corresponding to the two stereoisomers of the starting material, disappeared after 3 hours and were replaced with two new signals at 20.3/20.6 ppm corresponding to the two stereoisomers of DMT—$O^{5'}$—T—$O^{3'}$—PO (S—Pyr) —$O^{5'}$—T—$O^{3'}$-TBDMS.

0.2 mL of 3-dimethylpropylamine was added directly to the NMR tube. After about 1 hour, the 20.3/20.6 ppm signals had been replaced by two new signals at 9.1/8.8 ppm corresponding to the two stereoisomers of DMT—$O^{5'}$—T—$O^{3'}$—PO(NH—$(CH_2)_3$—$N(CH_3)_2$)—$O^{5'}$—T—$O^{3'}$—TBDMS. Thin layer chromatography analysis confirmed that only nucleotidic material comigrated with a genuine sample of the compound prepared by the method described in Example 1.

EXAMPLE 7

Effect of Cationic Phosphoramidate Linkage on Oligonucleotide Hybridization Properties The effect of cationic internucleoside linkages on hybridization properties of oligonucleotides was assessed using oligonucleotides having alternating anionic and cationic phosphoramidate linkages, the cationic linkages being stereoisomerically pure. Thus, the dimer block used to synthesize the cationic oligonucleotide was a stereoisomerically pure Tp(+)T dimer phosphoramidate prepared as described in Example 1. The point racemic $[Tp(+)Tp(-)]_7T$, wherein p(+) and p(−) are as defined above, was synthesized as described in Letsinger et al. (1988) *J. Am. Chem. Soc.* 110:4470–4471. Oligonucleotide analogs having the structure $[Tp(+)Tp(-)]_7T$ were synthesized on a solid support using either the pure stereoisomer of 5'—O—DMT—Tp(+)T-3'—P(N(iPr)$_2$)—O—$CH_2CH_2CN$ that eluted first or second from a silica gel column, or the point racemic mixture of the first- and second-eluting isomers, using standard phosphoramidite chemistry. The product of each synthesis was purified by RP-HPLC in the DMT form followed by detritylation with 80% aqueous acetic acid. The final product was lyophilized for storage.

The hybridization properties of the cationic homothymidine oligonucleotides containing alternating positive and negative linkages were assessed against poly (dA) and poly(A) target sequences. Thermal melt analyses were performed on a Perkin Elmer Lambda 2 UV/Vis spectrophotometer in 15 mM phosphate buffer, pH 7.3. The concentration of cationic oligonucleotide was approximately 5 μM. The changes in absorbance were measured at 260, 280 and 330 nm with a temperature ramping of 1° C./minute. The $T_m$ is the temperature corresponding to the midpoint of the region of maximum slope in a plot of the $A_{260}$ versus temperature.

The oligonucleotide sequences and the melting temperatures for duplex formation are shown in Tables 1 and 2.

TABLE 1

| $T_M$ OF $[Tp(+)Tp(-)]_7T$-POLY(dA) DUPLEXES | | | |
|---|---|---|---|
| OLIGOMER* | NO SALT | 0.1 M NaCl | 1.0 M NaCl |
| $[Tp(-)]_{14}$ | 25 | 35 | 53 |
| $[Tp(+)Tp(-)]_7T$ (first-eluting) | 56 | 57 | 57 |
| $[Tp(+)Tp(-)]_7T$ (second-eluting) | 22 | 23 | 40 |
| $[Tp(+)Tp(-)]_7T$ (point racemate) | 40 | 40 | 40 |

*Tp(+)T indicates a cationic dimethylaminopropylamido substituent on the internucleoside phosphorus atom and Tp(−)T indicates a conventional phosphodiester internucleoside linkage.

TABLE 2

$T_M$ OF [Tp(+)Tp(-)]$_7$T-POLY(A) DUPLEXES

| OLIGOMER* | NO SALT | 0.1 M NaCl | 1.0 M NaCl |
|---|---|---|---|
| [Tp(-)]$_{14}$ | 17 | 28 | 36 |
| [Tp(+)Tp(-)]$_7$T (first-eluting) | 37 | 39 | 41 |
| [Tp(+)Tp(-) ]$_7$T (second-eluting) | 18 | 20 | 20 |
| [Tp(+)Tp(-)]$_7$T (point racemate) | 29 | 30 | 31 |

*Tp(+)T indicates a cationic dimethylaminopropylamido substituent on the internucleoside phosphorus atom and Tp(-)T indicates a conventional phosphodiester internucleoside linkage.

The hybridization data in Tables 1 and 2 indicate that cationic oligonucleotides with stereoisomeric phosphoramidate linkages that correspond to the fast-eluting stereoisomer form very stable duplexes with DNA targets. In addition, these data shown that the duplex stability for the cationic oligonucleotides tested (first-eluting or point racemate) were essentially independent of salt concentration. This hybridization behavior is quite different from that of naturally occurring all-anionic oligonucleotides which form duplexes with their DNA target that are highly dependent upon the salt concentration. Generally, cationic oligonucleotides with stereoisomeric phosphoramidate linkages that correspond to the second-eluting stereoisomer do not form stable duplexes with DNA targets.

For example, in this experiment the $T_m$ for the normal all-anionic oligonucleotide-poly(dA) duplex decreased from 53° C. to 35° C. to 25° C. when the salt concentration was lowered from 1.0 M to 0.1 M to no added salt. In contrast, the cationic oligonucleotide prepared from the first-eluting Tp(+)T isomer had the highest $T_m$ values which were independent of the salt concentration. Even in the absence of salt, under which conditions a dramatic loss in duplex stability for the natural oligomer was observed, the $T_m$ value obtained with the cationic oligonucleotide prepared from the first-eluting Tp(+)T isomer was 56° C. The cationic oligonucleotide prepared from the second-eluting Tp(+)T isomer did not form a stable duplex with poly(dA) at no salt and 0.1 M NaCl. Even at 1.0 M NaCl the second-eluting isomer showed lower $T_m$ values than that prepared from the first-eluting isomer (-17° C.). The cationic oligonucleotide prepared from a point racemic mixture of Tp(+)T formed duplexes with intermediate stability at no and low salt concentrations; however, the $T_m$ values for the point racemate were salt-independent and when no added salt was present, the $T_m$ values obtained with the point racemate was greater than the all anionic oligonucleotide.

As reflected by the higher $T_m$ values, duplex stability with a poly(A) target was higher for the first-eluting cationic oligomer than for the all-anionic oligomer. The second-eluting isomer did not form stable duplexes with poly(A) while the point racemate showed intermediate duplex stability.

EXAMPLE 8

Effect of Cationic Phosphotriester Linkage on Oligonucleotide Hybridization Properties Three thymidine oligonucleotides were prepared having: (1) all standard phosphodiester internucleoside linkages (5'-TTTTTTTTTTTTTTT-3')(SEQ ID NO: 1); (2) alternating anionic standard PDE linkages and cationic phosphoramidate internucleoside linkages, wherein the cationic N-substituent group is dimethylaminopropyl (designated [Tp(N+)Tp(-)]$_7$T) (Letsinger et al. (1988) *J. Am. Chem. Soc.* 110:4471–4472); and (3) alternating standard PDE linkages and cationic phosphotriester internucleoside linkages, wherein the cationic substituent group is dimethylaminopropyl (designated "[Tp(O+)Tp(-)]$_7$T") (synthesized on a solid support using standard phosphoramidite chemistry).

The hybridization properties of the cationic homothymidine oligonucleotides containing alternating positive and negative linkages were assessed against poly (dA) as described in Example 7. The results are shown in Table 3.

TABLE 3

$T_M$ OF Thymidine Oligomer-POLY(dA) DUPLEXES

| Thymidine Oligomer | No NaCl | 0.1 M NaCl |
|---|---|---|
| 5'-TTTTTTTTTTTTTTT-3' (SEQ ID NO:1) | 25 | 37 |
| [Tp(N+)Tp(-)]$_7$T | 35 | 36 |
| [Tp(O+)Tp(-)]$_7$T | 46 | 47 |

The data in Table 3 show that the [Tp(O+)Tp(-)]$_7$T oligomer has a $T_m$ that is independent of salt concentration and is 10° C. (0.1 M NaCl) and 21° C. (no NaCl) higher than the all anionic thymidine 15-mer. In addition, the [Tp(O+)Tp(-)]$_7$T oligomer forms a more stable duplex with poly (dA) than the [Tp(N+)Tp(-)]$_7$T oligomer.

EXAMPLE 9

Hybridization of Thymidine and 2'—O— Methyluridine Zwitterionic Derivatives to a Duplex Target The hybridization of zwitterionic thymidine and 2'—O—methyluridine derivatives to a duplex target d($T_{15}C_4A_{15}$) was studied to show the utility of such oligonucleotides as probes for double-stranded DNA. In the absence of other oligomers, d($T_{15}C_4A_{15}$) forms a self-complementary structure with a dT.dA stem of high stability ($T_m$ 62° C. in 0.1 M NaCl; $T_m$ 78° C. in 1 M NaCl). All stereouniform zwitterionic oligomers were prepared using the procedures described in Examples 1 through 6 above or as described in Horn et al. (1996) *Tetrahedron Lett.* 37:743–745 and Chaturvedi et al. (1996) *Nucleic Acids Res.* 24:2318–2323. As above, the stereoisomer having the higher $R_f$ is designated herein the "first-eluting" isomer while the stereoisomer having the lower $R_f$ is designated herein the "second-eluting" isomer.

The affinities of the oligothymidylate derivatives for the duplex target d($T_{15}C_4A_{15}$) depend strongly on the charge and stereochemistry of the probe and the ionic strength of the solution (Table 4). One of the zwitterionic isomers, d(T+T-)$_7$T (first-eluting), formed a relatively stable triple-stranded complex with the target even in 0.1 M NaCl. The melting curve for an equimolar mixture of d(T+T-)$_7$T (first-eluting) and d($T_{15}C_4A_{15}$) showed a transition ($T_m$ 24° C.) for dissociation of the zwitterionic strand from the duplex segment, as well as a transition ($T_m$ 68° C.) for denaturation of d($T_{15}C_4A_{15}$); and a plot of $A_{260}$ versus titrant for titration of d(T+T-)$_7$T (first-eluting) with d($T_{15}C_4A_{15}$) at 0° C. displayed a break at equimolar concentrations of the two oligomers (data not shown), in accord for a complex with the dT.dA.dT motif. Under the same conditions, neither dT$_{15}$ nor the zwitterionic isomeric oligomer d(T+T-)$_7$T (second-eluting) interacted significantly with d($T_{15}C_4A_{15}$). In a high salt solution (1.0 M NaCl) dT$_{15}$ did bind to d($T_{15}C_4A_{15}$) ($T_m$ 30° C.). The stability of the complex formed by d(T+T-)$_7$T (first-eluting) also increased with an increase in the salt concentration ($T_m$ 32° C. in 1.0 M NaCl); however, the rise in $T_m$ was less than in the case of the all anionic probe. Oligomer d(T+T-)$_7$T (second-eluting) did not bind significantly to d($T_{15}C_4A_{15}$) even in 1 M NaCl.

Since it has been shown that replacement of thymidine by 2'—O—methyluridine in a phosphodiester oligonucleotide probe enhances stability of triple-stranded complexes formed with the probe (Escude et al. (1992) C. R. *Acad. Sci. Paris III*, 315:521–525). The stereoisomeric oligomers (U'+U'-)$_7$dT (first-eluting) and (U'+U'-)$_7$dT (second-eluting) were prepared to test the effect of this substitution on binding of zwitterionic oligonucleotides to double-stranded targets. (U'+U'-)$_7$dT (first-eluting) bound to d($T_{15}C_4A_{15}$) more effectively ($T_m$ 35° C., 0.1 M NaCl) than the thymidine analogue, d(T+T-)$_7$T (first-eluting), ($T_m$ 24° C., 0.1 M NaCl). Neither the isomeric oligomer, (U'+U'-)$_7$dT (second-eluting), nor the corresponding phosphodiester control, U'$_{14}$dT, interacted significantly with d($T_{15}C_4A_{15}$) under these conditions. In contrast to the results for the triple-stranded complexes, the 2'—O—methyluridine derivative, (U'+U'-)$_7$dT (first-eluting), was found to bind less effectively than the thymidine analogue, d(T+T-)$_7$T (first-eluting) to an equivalent of poly(dA). The $T_m$ values for formation of the double-stranded complex in 0 M NaCl, 0.1 M NaCl, and 1.0 M NaCl solutions were, respectively, 35° C., 36° C., and 41° C. for (U'+U'-)$_7$dT (first-eluting); and 58° C., 58° C., and 58° C. for d(T+T-)$_7$T (first-eluting) (see Horn et al. *Tetrahedron Lett.*, supra).

TABLE 4

$T_M$ VALUES (°C.) FOR DISSOCIATION OF TRIPLE-STRANDED COMPLEXES FORMED FROM SINGLE STRANDED PROBES AND TARGET d($T_{15}C_4A_{15}$), 3.3 mM EACH AT pH 7.0

| Oligomer | 0.1 M NaCl | 1.0 M NaCl |
|---|---|---|
| d(T+T-)$_7$T (first-eluting) | 24 | 32 |
| d(T+T-)$_7$T (first-eluting) | <0 | <5 |
| dT$_{15}$ | <0 | <30 |
| (U'+U'-)$_7$dT (first-eluting) | 35 | 42 |
| (U'+U'-)$_7$dT (second-eluting) | — | <10 |
| U'$_{14}$dT | <5 | 40 |
| d(T+T-)2(T+C-)$_5$T (first-eluting) | <0 | <5 |

Data for the mixed dT,dC oligomers d(T+T-)$_2$(T+C-)$_5$T (first-eluting) and d(T+T-)$_2$(T+C-)$_5$T) (second-eluting) are presented in Table 5. The target d[A$_5$(GA)$_5$T$_4$(TC)$_5$T$_5$], self-associates under the conditions employed ($T_m$ 68° C. at pH 7.0 and $T_m$ 67° C. at pH 6.0; 0.1 M NaCl). The dT,dC pentadecamers bound to d[A$_5$(GA)$_5$T$_4$(TC)$_5$T$_5$] with higher affinity than the dT or dU' pentadecamers bound to d($T_{15}C_4A_{15}$), and, as expected for triple-stranded structures containing dC (Lipsett, M. N., *J. Biol. Chem.* 239:1256–1260 (1964)), the affinity was greater at pH 6 than at pH 7. The thermal stability of the triple-stranded complex formed by one of the zwitterionic probes, d(T+T-)$_2$(T+C-)$_5$Tb (first-eluting), and target d[A$_5$(GA)$_5$T$_4$(TC)$_5$T$_5$] in a low salt solution (0.1 M NaCl) at pH 7. The $T_m$ value was 23° C. higher than that for the complex formed by the corresponding all-phosphodiester probe. That the high affinity of the zwitterionic oligonucleotides depends on sequence as well as ionic charge and stereochemistry at phosphorus was demonstrated by experiments in which d(T+T-)$_7$T (first-eluting) was paired with a mismatched target, d[A$_5$(GA)$_5$T$_4$(TC)$_5$T$_5$], and d(T+T-)$_2$(T+C-)$_5$Tb (first-eluting) was similarly paired with d($T_{15}C_4A_{15}$). Neither of these systems afforded stable-triple stranded complexes (Tables 4 and 5).

TABLE 5

$T_M$ VALUES (°C.) FOR DISSOCIATION OF TRIPLE-STRANDED COMPLEXES FORMED FROM SINGLE STRANDED PROBES AND TARGET d[A$_5$(GA)$_5$T$_4$(TC)$_5$T$_5$], EACH 5 mM IN 0.1 M NaCl.

| Oligomer | 0.1 M NaCl | 1.0 M NaCl |
|---|---|---|
| d(T+T-)$_2$(T+C-)$_5$T (first-eluting) | 42 | 52 |
| d(T+T-)$_2$(T+C-)$_5$T (second-eluting) | 11 | 37 |
| dT$_5$(CT)$_5$ | 19 | 45 |
| d(T+T-)$_7$T (first-eluting) | <0[a] | 42 |

[a]Also <0° C. in 1.0 M NaCl.

Three pairs of stereoisomeric zwitterionic 15mers were prepared for this study. A first pair was derived from thymidine, a second pair from 2'—O—methyluridine and a third pair from thymidine and deoxycytidine. In each case, all phosphoramidate linkages in a given oligomer had the same configuration. Thermal denaturation experiments showed that participation of these alternating cationic-anionic oligonucleotides in formation of triple-stranded complexes is highly dependent on chirality at the modified phosphate linkages.

In each case one of the stereoisomeric probes, designated as the first-eluting isomer, binds more effectively to a complementary double-stranded DNA target than the corresponding all phosphodiester probe does. In 0.1 M aqueous NaCl at pH 7, the enhancement in $T_m$ is of the order of 20° C. for the dT and the dT,dC zwitterionic 15 mers (d(T+T-)$_7$T (first-eluting) and d(T+T-)$_2$(T+C-)$_5$T (first-eluting)) and ~35° C. for the 2'—O—methyluridine derivative ((U'+U'-)$_7$dT (first-eluting)). The enhancement in $T_m$ in 1 M NaCl solutions is less, but still significant. It is noteworthy that the affinity of d(T+T-)$_2$(T+C-)$_5$T (first-eluting) is relatively high at pH 7, even though the probe contains several dC units. Strong binding of this unsymmetrical, mixed-base probe to the double-stranded target is consistent with a structure in which the third strand is oriented parallel to the purine strand, as in other triple-stranded complexes derived from two pyrimidine and one purine strand.

In contrast to the results with the first-eluting stereoisomeric oligomers, the phosphoramidate oligomers with the opposite configuration at phosphorus (second-eluting) exhibited very low affinity for the double-stranded targets. Since the absolute configuration of the isomers has not yet been definitively assigned, and structural information on the geometry of the triple strand complex is limited, speculation on the reasons for these differences is premature. It is interesting, however, that the configuration at the phosphoramidate links that favors binding of an oligonucleotide probe to double-stranded DNA is the same that favors binding to a single-stranded target to give a double-stranded complex (Horn et al. *Tetrahedron Lett.*, supra).

Gryaznov et al. have shown that oligodeoxyribonucleotide N3'-P5' phosphoramidate derivatives bind to DNA duplexes to give unusually stable pyr.pur.pyr and pur.pur.pyr complexes (Gryaznov et al. (1994) *J. Am. Chem.*

Soc. 116:3143–3144 and Gryaznov et al. (1995) Proc. Natl. Acad. Sci. USA, 92:5798–580). Nielsen et al. have found that 'peptide nucleic acids' (PNAs) interact with appropriate DNA sequences by strand invasion to give PNA.pur.PNA triple-stranded segments (Nielsen et al. (1991) Science 254:1497–1500; Cherny et al. (1993) Proc. Natl. Acad. Sci. USA 90:1667–1670; and Nielsen et al. (1993) Nucleic Acids Res. 21:197–200). The stereo-uniform cationic phosphoramidate derivatives comprise another family of oligonucleotide analogues that bind strongly to double stranded DNA targets. Since these three families differ from one another in physical and chemical properties and, no doubt, in behavior in biological systems as well, they offer the chemist rich opportunities for tailoring DNA binding agents for specific applications.

EXAMPLE 10

Horn et al. Tetrahedron Lett, supra previously noted an unusual feature in the melting curve obtained at 260 nm for a 1/1 dT/dA mixture of d(T+T-)$_7$T (second-eluting) and poly(dA) in 1 M NaCl solution. The melting curve showed two transitions, differing in $T_m$ by ~20° C. The first transition appears to stem from a reversible disproportionation of two d(T+T-)$_7$T (second-eluting).poly(dA) duplex segments to give a triplex with the dA.dA.dT motif plus a strand of d(T+T-)$_7$T (second-eluting), and that the second transition represents reversible dissociation of the triplex to give free poly(dA) and d(T+T-)$_7$T (second-eluting). Several lines of evidence support this conclusion.

(i) Two transitions appear in the melting curve measured at 280 nm as well as the one at 260 nm (see Chaturvedi et al. Nucleic Acids Res, supra). The higher temperature transition in the 280 nm curve is hypochromic. Characteristically, transitions for dissociation of dT.dA duplexes and dT.dA.dT triplexes are hyperchromic at these wavelengths. This result points to dissociation of a complex with a novel structure.

(ii) Melting curves obtained in low salt solutions (0–0.1 M NaCl) showed a single transition (~$T_m$ 22° C.) that was independent of the salt concentration. As the salt concentration was increased incrementally, a second transition appeared at progressively higher temperatures. The salt dependence for the second transition is consistent with expectations for dissociation of a triple-stranded complex containing a zwitterionic and two anionic strands.

(iii) Association curves obtained by cooling solutions of the oligomers slowly from 80° C. to 0° C. demonstrated that the transitions are fully reversible. As a further test, a 1dT/1dA mixture of d(T+T-)$_7$T (second-eluting) and poly (dA) in 1 M NaCl was allowed to cool from 80° C. to 25° C. and held at the lower temperature for two hours to permit a slow equilibration to take place. No change in absorbance occurred during the two hours, indicating that the system was stable at this temperature. When the temperature was then further reduced through the range for the lower transition to 18C, the absorbance at 260 nm dropped rapidly and equilibrium was reached within two minutes.

(iv) A single transition ($T_m$ 42° C.; 1 M NaCl) was observed on heating a mixture of d(T+T-)$_7$T (second-eluting) and poly(dA) at a 1dT/2dA nucleotide ratio from 0° C. to 80° C., demonstrating that the triple-stranded complex was stable at 0° C. in absence of excess d(T+T-)$_7$T (second-eluting).

(v) In agreement with these results, titration of d(T+T-)$_7$T (second-eluting) in 1 M NaCl (pH 7.0) with poly(dA) consumed twice as much poly(dA) at 30° C. as at 0° C., and the breaks corresponded to formation of a 1dT/2dA complex at 30° C. and a 1dT/1dA complex at 0° C. As controls, $dT_{15}$ was also titrated with poly(dA) under the same conditions. These experiments showed breaks corresponding to 2dT/1dA, 1dT/1dA and 1dT/1dA, as expected, for titrations at 0° C. in 1.0 M NaCl, 30° C. in 1.0 M NaCl and 0° C. in 0.1 M NaCl, respectively. Also, titration of d(T+T-)$_7$T (second-eluting) at 0° C. in 0.1 M NaCl gave a 1dT/1dA ratio.

(vi) A single transition ($T_m$ 26° C.) was found on heating a mixture of d(T+T-)$_7$T (second-eluting) with either one or two equivalents of d(CCA$_{15}$CC) in 1.0 M NaCl. This result suggested that appearance of the second transition in the case of poly(da) might be related to the fact poly(da) could fold to a hairpin structure that would stabilize a dA.dA.dT triple-stranded complex. We therefore examined hybridization of d(T+T-)$_7$T (second-eluting) with a shorter, well defined oligomer, d(A$_{15}$C$_4$A$_{15}$), which also could fold to a hairpin structure. This target indeed simulated poly(dA) in behavior, although the complexes formed were somewhat less stable ($T_m$~17° C. for the disproportionation reaction and ~32° C. for dissociation of the triplex in 1.0 M NaCl; see Chaturvedi et al. Nucleic Acid Res., supra). A comparison with the heating curve for d(A$_{15}$C$_4$A$_{15}$) alone showed that these breaks indeed reflect interaction of d(T+T-)$_7$T (second-eluting) with this target oligonucleotide. As in the case with poly(dA), the transitions were reversible.

Formation of two distinct complexes from d(T+T-)$_7$T (second-eluting) and poly(dA) is further supported by CD spectral data (see Chaturvedi et al. Nucleic Acids Res., supra). The CD spectrum for a mixture of d(T+T-)$_7$T (second-eluting) and poly(dA) containing equivalent concentrations of dT and dA units in 1 M NaCl at 5° C. is very similar to the CD spectrum for the same combination of d(T+T-)$_7$T (second-eluting) and poly(dA) in 0.1 M NaCl and for the spectra of poly(dT).poly(dA) in 0.1 M and in 1 M NaCl. The two peaks and the trough observed in the 255–300 nm region are distinctive (Wells et al. (1970) J. Mol. Biol. 54:465–497) and serve as a signature for the poly(dT).poly(dA) duplex. The similarity in the spectra for all these systems indicates that the base stacking is much the same in all cases. These data therefore point to a conventional duplex structure for the complex derived from d(T+T-)$_7$T (second-eluting) and poly(dA) in 1 M NaCl at 5° C. A very different spectrum was obtained when the solution of d(T+T-)$_7$T (second-eluting) and poly(da) was warmed to 27° C. The trough at 247 nm deepened, the peak at 259 nm fell, the trough at 268 nm disappeared, and the peak at 282 nm increased. When the solution was then cooled, the spectrum obtained at 27° C. readily reverted to the spectrum obtained at 0° C. These changes correlate well with the UV absorbance changes observed on heating and cooling the solution. Furthermore, the spectrum obtained at 27° C. is quite different from the spectrum expected for a mixture of free d(T+T-)$_7$T (second-eluting)and poly(dA). We attribute the spectrum obtained at 27° C. to the presence of a dA.dA.dT triple stranded complex derived from poly(dA) and d(T+T-)$_7$T (second-eluting). This assignment leads to the prediction that the CD spectrum of a 2dA/1dT ratio of poly(dA) and d(T+T-)$_7$T (second-eluting) in 1 M NaCl at 27° C. would be similar to the spectrum obtained for a 1dA/dT ratio of poly(dA) and d(T+T-)$_7$T (second-eluting) at 27° C. and that it would remain unchanged on cooling to 5° C. These results were indeed observed.

The CD spectrum for a 1dT/1dA mixture of oligomer d(T+T-)$_7$T (first-eluting) and poly(dA) in 1 M NaCl at 27° C. is very similar to the spectrum of the poly(dT).poly(dA) duplex. In contrast to the case with d(T+T-)$_7$T (second-eluting), no evidence for formation of a dA.dA.dT triplex was found. The CD spectrum was virtually unchanged on cooling to 5° C. and was not altered significantly by addition of a second equivalent of poly(dA). These results buttress data from the melting curves indicating that d(T+T-)$_7$T (first-eluting) forms a duplex, but not a dA.dA.dT triplex, with poly(dA).

A surprising set of equilibria was found for systems containing the second-eluting d(T+T-)$_7$T isomer and poly (dA) or d(A$_{15}$C$_4$A$_{15}$) in 1 M NaCl solution. For a system containing the second-eluting d(T+T-)$_7$T isomer and poly (dA) in a 1dT/1dA ratio, at 0° C. the components form a double-stranded complex; at 30° C. they exist as a dA.dA.dT triple-stranded complex and an equivalent of free d(T+T-)$_7$T (second-eluting); and at 50° C. the complex is fully dissociated. The transitions between the states are relatively sharp (T$_m$ 22° C. and T$_m$ 420° C.) and equilibrium is established rapidly both on heating and cooling the solution.

The system involving d(A$_{15}$C$_4$A$_{15}$) fits the same scheme, but with a dC$_4$ strand serving as the linker to facilitate alignment of two dA$_{15}$ segments. The importance of the configuration of the phosphoramidate linkages is shown by the fact that oligomer d(T+T-)$_7$T (first-eluting), in contrast to d(T+T-)$_7$T (second-eluting), did not form triple stranded complexes of this type.

Two features in these equilibria are unusual, though not without some related precedents: (i) formation of a stable triple-stranded complex containing exclusively dA.dA.dT triads; and (ii) formation of a triple-stranded complex by a thermally induced disproportionation of a double-stranded complex. Although a number of examples of pur.pur.pyr triplexes have been reported (see Lipsett (1964) *J. Biol. Chem.* 239:1256–1260; Anna et al. (1989) *Science* 241:456–459; Beal et al. (1992) *Nucleic Acids Res.* 20:2773–2776; and Pilch et al. (1991) *Biochemistry* 30:6081–6087 for representative cases), the stable complexes containing dA.dA.dT triads that have been described have also contained dG units in one of the purine strands. Pilch et al. have noted that " . . . the presence of guanine residues appears to be crucial for stabilization of short pur.pur.pyr triplexes" (Pilch et al. *Biochemistry*, supra). For the ribonucleotide family, however, Broitman et al. (1987) *Proc. Natl. Acad. Sci. USA* 84:5120–5124 have described a triple-stranded complex, poly(A).poly(A).poly(U), which can form when the degree of polymerization of poly(A) falls in the range of ~28–150, and Lauceri et al. (1996) *Angew. Chem. Int. Ed. Engl.* 35:215–216 have shown that cationic porphyrins in low concentration induce formation of poly (A).poly(A).poly(U) triple-stranded complexes from high molecular weight poly(A) (>400 bp). With respect to thermally induced disproportions, examples affording pyr.pur.pyr complexes have been reported for both ribonucleotide, [poly(A).poly(U)] (Miles et al. (1964) *Biochem. Biophys. Res. Comm.* 14:129–136; Stevens et al. (1964) *Biopolymers* 2:293–314; and Broitman et al. *Proc. Natl. Acad. Sci. USA*, supra, and deoxyribonucleotide polymers, [poly(dTdC).poly(dGdA)] (Lee et al. (1979) *Nucleic Acids Res.* 6:3073–3091; Lee et al. (1984) *Nucleic Acids Res.* 12:6603–6613; and Hampel et al. (1991) *Biochemistry* 30:4455–4459).

It appears that the unusual stability of the dA.dA.dT complexes containing oligonucleotide d(T+T-)$_7$T (second-eluting), and the disproportionation reaction leading to their formation, must reflect the presence of the stereouniform side chains in the probe. The properties of zwitterionic oligomers with this chirality may prove useful in designing novel self-assembly systems based on oligonucleotide hybridization.

---

---

We claim:

1. A composition comprising molecules of an oligonucleotide having at least one cationic internucleoside linkage having the structure (I)

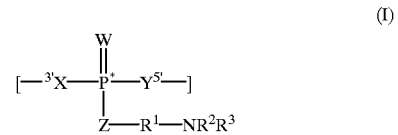

wherein:
  W is selected from the group consisting of O, S and Se;
  X and Y are independently selected from the group consisting of (i) O, (ii) S, (iii) C(R$^4$)R$_5$ where R$^4$ and R$^5$ are independently selected from the group consisting of H and C$_1$–C$_6$ alkyl, and (iv) NR$^6$ where R$^6$ is H or C$_1$–C$_6$ alkyl;
  Z is selected from the group consisting of O, S, C$_1$–C$_6$ alkylene, C$_2$–C$_6$ alkenylene, C$_2$–C$_6$ alkynylene and NR$^7$ where R$^7$ is H or C$_1$–C$_6$ alkyl, with the proviso that when W, X and Y are O, Z is O, S or NR$^7$;
  R$^1$ is selected from the group consisting of C$_1$–C$_6$ alkylene, C$_2$–C$_6$ alkenylene, C$_2$–C$_6$ alkynylene, monocyclic arylene and a bond;
  R$^2$ and R$^3$ are independently selected from the group consisting of H, C$_1$–C$_6$ alkyl, C$_1$–C$_6$ alkyl substituted with 1 to 4 NH$_2$ groups, and monocyclic aryl, or R$^2$ and R$^3$ may be linked to form a five- or six-membered alkyl or aryl ring or an N-, O- or S-containing heterocycle; and wherein P* represents an asymmetric phosphorus atom capable of existing in two distinct stereoisomeric configurations, and further wherein the linkage is stereouniform among the molecules of the oligonucleotide.

2. The composition of claim 1, wherein the stereoisomeric configuration of the cationic internucleoside linkage corresponds to the configuration of the first-eluted stereoisomer when a point racemic mixture of a nucleotide dimer containing the internucleoside linkage is resolved using silica gel column chromatography.

3. The composition of claim 1, wherein the stereoisomeric configuration of the cationic internucleoside linkage corresponds to the configuration of the second-eluted stereoisomer when a point racemic mixture of a nucleotide dimer containing the internucleoside linkage is resolved using silica gel column chromatography.

4. The composition of claim 2, wherein Z is $NR^7$.

5. The composition of claim 4, wherein $R^7$ is H.

6. The composition of claim 4, wherein X and Y are O.

7. The composition of claim 4, wherein $R^1$ is $C_1$–$C_6$ alkylene.

8. The composition of claim 7, wherein $R^1$ is $(CH_2)_3$.

9. The composition of claim 4, wherein $R^2$ and $R^3$ are $C_1$–$C_6$ alkyl.

10. The composition of claim 9, wherein $R^2$ and $R^3$ are $CH_3$.

11. The composition of claim 4, wherein W is S.

12. The composition of claim 1, wherein Z is $NR^7$.

13. The composition of claim 12, wherein $R^7$ is H.

14. The composition of claim 12, wherein $R^1$ is $C_1$–$C_6$ alkylene.

15. The composition of claim 14, wherein $R^1$ is $(CH_2)_2$.

16. The composition of claim 12, wherein $R^2$ and $R^3$ are $C_1$–$C_6$ alkyl substituted with 1 to 4 $NH_2$ groups.

17. The composition of claim 16, wherein $R^2$ and $R^3$ are —$CH_2CH_2NH_2$.

18. A composition comprising molecules of an oligonucleotide having alternating cationic and anionic internucleoside linkages wherein the cationic internucleoside linkages have the structure (II)

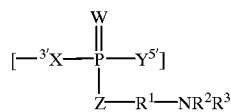

(II)

wherein:
W is selected from the group consisting of O, S and Se;
X and Y are independently selected from the group consisting of (i) O, (ii) S, (iii) $C(R^4)R^5$ where $R^4$ and $R^5$ are independently selected from the group consisting of H and $C_1$–$C_6$ alkyl, and (iv) $NR^6$ where $R^6$ is H or $C_1$–$C_6$ alkyl;
Z is selected from the group consisting of O, S, $C_1$–$C_6$ alkylene, $C_2$–$C_6$ alkenylene, $C_2$–$C_6$ alkynylene and $NR^7$ where $R^7$ is H or $C_1$–$C_6$ alkyl, with the proviso that when W, X and Y are O, Z is O or S;
$R^1$ is selected from the group consisting of $C_1$–$C_6$ alkylene, $C_2$–$C_6$ alkenylene, $C_2$–$C_6$ alkynylene, monocyclic arylene and a bond;
$R^2$ and $R^3$ are independently selected from the group consisting of H, $C_1$–$C_6$ alkyl, $C_1$–$C_6$ alkyl substituted with 1 to 4 $NH_2$ groups, and monocyclic aryl, or wherein $R^2$ and $R^3$ are linked to form a five- or six-membered alkyl or aryl ring or N-, O- or S-containing heterocycle; and wherein P is a phosphorus atom that may or may not be capable of existing in two distinct stereoisomeric configurations and further wherein the linkage may or may not be stereouniform among the molecules of the oligonucleotide.

19. A method for making a composition comprising molecules of an oligonucleotide containing at least one cationic internucleoside linkage having the structure (I)

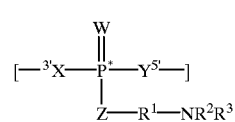

(I)

wherein:
W is selected from the group consisting of O, S and Se;
X and Y are independently selected from the group consisting of (i) O, (ii) S, (iii) $C(R^4)R^5$ where $R^4$ and $R^5$ are independently selected from the group consisting of H and $C_1$–$C_6$ alkyl, and (iv) $NR^6$ where $R^6$ is H or $C_1$–$C_6$ alkyl;
Z is selected from the group consisting of O, S, $C_1$–$C_6$ alkylene, $C_2$–$C_6$ alkenylene, $C_2$–$C_6$ alkynylene and $NR^7$ where $R^7$ is H or $C_1$–$C_6$ alkyl, with the proviso that when W, X and Y are O, Z is O, S or $NR^7$;
$R^1$ is selected from the group consisting of $C_1$–$C_6$ alkylene, $C_2$–$C_6$ alkenylene, $C_2$–$C_6$ alkynylene, monocyclic arylene and a bond;
$R^2$ and $R^3$ are independently selected from the group consisting of H, $C_1$–$C_6$ alkyl, $C_1$–$C_6$ alkyl substituted with 1 to 4 $NH_2$ groups, and monocyclic aryl, or $R^2$ and $R^3$ may be linked to form a five- or six-membered alkyl or aryl ring or an N-, O- or S-containing heterocycle; and
wherein P* represents an asymmetric phosphorus atom capable of existing in two distinct stereoisomeric configurations,
and further wherein the linkage is stereouniform among the molecules of the oligonucleotide, said method comprising:
(a) synthesizing a point racemic mixture of protected cationic nucleotide dimers comprising the cationic internucleoside linkage and a 3'—O—t-butyldimethyldisilyl protecting group;
(b) optionally resolving the stereoisomers in the mixture;
(c) deprotecting the cationic nucleotide dimer isolated in step (b);
(d) converting the deprotected cationic nucleotide dimer provided in step (c) into the corresponding 3'—O—$CH_2CH_2CN$ phosphoramidite derivative by reaction with Cl—$P(N(iPr)_2)$—O—(β-cyanoethyl); and
(e) coupling the 3'—O—$CH_2CH_2CN$ phosphoramidite derivative to an unprotected hydroxyl-containing terminal unit of an oligonucleotide chain.

20. The composition of claim 18, wherein Z is $NR^7$.

21. The composition of claim 20, wherein $R^7$ is H.

22. The composition of claim 20, wherein X and Y are O.

23. The composition of claim 20, wherein $R^1$ is $C_1$–$C_6$ alkylene.

24. The composition of claim 23, wherein $R^1$ is $(CH_2)_3$.

25. The composition of claim 20, wherein $R^2$ and $R^3$ are $C_1$–$C_6$ alkyl.

26. The composition of claim 25, wherein $R^2$ and $R^3$ are $CH_3$.

27. The composition of claim 20, wherein W is S.

28. The composition of claim 20, wherein $R^1$ is $C_1$–$C_6$ alkylene.

29. The composition of claim 28, wherein $R^1$ is $(CH_2)_2$.

30. The composition of claim 20, wherein $R^2$ and $R^3$ are $C_1$–$C_6$ alkyl substituted with 1 to 4 $NH_2$ groups.

31. The composition of claim 30, wherein $R^2$ and $R^3$ are —$CH_2CH_2NH_2$.

32. A composition comprising molecules of an oligonucleotide having at least one cationic internucleoside linkage having the structure (I)

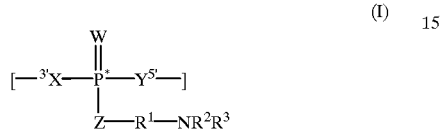

wherein:
  W is S;
  X and Y are O;
  Z is NH;
  $R^1$ is $(CH_2)_3$;
  $R^2$ and $R^3$ are $CH_3$; and
  wherein P* represents an asymmetric phosphorus atom, such that the linkage exists in stereoisomeric configuration that corresponds to the configuration of the first-eluted stereoisomer when a point racemic mixture of a nucleotide dimer containing the internucleoside linkage is resolved using silica gel column chromatography.

33. A nucleic acid hybridization assay comprising:
(a) providing a labeled oligonucleotide probe containing at least one cationic stereouniform internucleoside linkage, wherein the cationic internucleoside linkage has the structure (I)

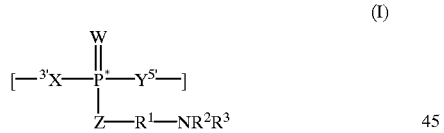

wherein
  W is selected from the group consisting of O, S and Se,
  X and Y are independently selected from the group consisting of (i) O, (ii) S, (iii) $C(R^4)R^5$ where $R^4$ and $R^5$ are independently selected for the group consisting of H and $C_1$–$C_6$ alkyl, and (iv) $NR^6$ where $R^6$ is H or $C_1$–$C_6$ alkyl,
  Z is selected from the group consisting of O, S, $C_1$–$C_6$ alkylene, $C_2$–$C_6$ alkenylene, $C_2$–$C_6$ alkynylene and $NR^7$ where $R^7$ is H or $C_1$–$C_6$ alkyl, with the proviso that when W, X and Y are O, Z is O, S or $NR^7$,
  $R^1$ is selected from the group consisting of $C_1$–$C_6$ alkylene, $C_2$–$C_6$ alkenylene, $C_2$–$C_6$ alkynylene, monocyclic arylene and a bond,
  $R^2$ and $R^3$ are independently selected from the group consisting of H, $C_1$–$C_6$ alkyl, $C_1$–$C_6$ alkyl substituted with 1 to 4 $NH_2$ groups, and monocyclic aryl, or $R^2$ and $R^3$ may be linked to form a five- or six-membered alkyl or aryl ring or an N-, O- or S- containing heterocycle, and wherein P* represents and asymmetric phosphorus atom capable of existing in two distinct stereoisomeric configurations;
(b) hybridizing the probe to a single-stranded analyte nucleic acid to produce a labeled duplex; and
(c) detecting the labeled duplex.

34. A nucleic acid hybridization assay comprising:
(a) providing a labeled oligonucleotide probe containing at least one cationic internucleoside linkage, wherein the cationic internucleoside linkage has the structure (II)

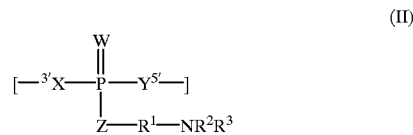

wherein:
  W is selected from the group consisting of O, S and Se;
  X and Y are independently selected from the group consisting of (i) O, (ii) S, (iii) $C(R^4)R^5$ where $R^4$ and $R^5$ are independently selected from the group consisting of H and $C_1$–$C_6$ alkyl, and (iv) $NR^6$ where $R^6$ is H or $C_1$–$C_6$ alkyl;
  Z is selected from the group consisting of O, S, $C_1$–$C_6$ alkylene, $C_2$–$C_6$ alkenylene, $C_2$–$C_6$ alkynylene and $NR^7$ where $R^7$ is H or $C_1$–$C_6$ alkyl, with the proviso that when W, X and Y are O, Z is O or S;
  $R^1$ is selected from the group consisting of $C_1$–$C_6$ alkylene, $C_2$–$C_6$ alkenylene, $C_2$–$C_6$alkynylene, monocyclic arylene and a bond; and
  $R^2$ and $R^3$ are independently selected from the group consisting of H, $C_1$–$C_6$ alkyl, $C_1$–$C_6$ alkyl substituted with 1 to 4 $NH_2$ groups, and monocyclic aryl, or wherein $R^2$ and $R^3$ are linked to form a five- or six-membered alkyl or aryl ring or N-, O- or S-containing heterocycle;
(b) hybridizing the probe to a single-stranded analyte nucleic acid to produce a labeled duplex; and
(c) detecting the labeled duplex.

35. The nucleic acid hybridization assay of claim 33, wherein the oligonucleotide probe has alternating cationic and anionic internucleoside linkages.

36. The nucleic acid hybridization assay of claim 33, wherein the cationic internucleoside linkages have the structure (II)

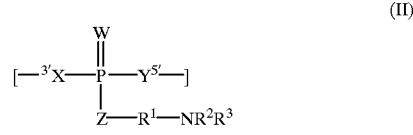

wherein:
  W is selected from the group consisting of O, S and Se;
  X and Y are independently selected from the group consisting of (i) O, (ii) S, (iii) $C(R^4)R^5$ where $R^4$ and $R^5$ are independently selected from the group consisting of H and $C_1$–$C_6$ alkyl, and (iv) NR6 where $R^6$ is H or $C_1$–$C_6$ alkyl;
  Z is selected from the group consisting of O, S, $C_1$–$C_6$ alkylene, $C_2$–$C_6$ alkenylene, $C_2$–$C_6$ alkynylene and $NR^7$ where $R^7$ is H or $C_1$–$C_6$ alkyl, with the proviso that when W, X and Y are O, Z is O or S;

$R^1$ is selected from the group consisting of $C_1$–$C_6$ alkylene, $C_2$–$C_6$ alkenylene, $C_2$–$C_6$ alkynylene, monocyclic arylene and a bond; and $R^2$ and $R^3$ are independently selected from the group consisting of H, $C_1$–$C_6$ alkyl, $C_1$–$C_6$ alkyl substituted with 1 to 4 $NH_2$ groups, and monocyclic aryl, or wherein $R^2$ and $R^3$ are linked to form a five- or six-membered alkyl or aryl ring or N-, O- or S-containing heterocycle.

* * * * *

UNITED STATES PATENT AND TRADEMARK OFFICE
CERTIFICATE OF CORRECTION

PATENT NO. : 6,017,700
DATED : January 25, 2000
INVENTOR(S) : Thomas Horn et al.

It is certified that error appears in the above-identified patent and that said Letters Patent is hereby corrected as shown below:

On the patent cover page, item [73] Assignee, please replace "Bayer Corporation, East Walploe, Mass.," with —Bayer Corporation, East Walpole, Mass. and Northwestern University, Evanston, Ill.—.

Signed and Sealed this

Fifth Day of June, 2001

*Attest:*

*Attesting Officer*

NICHOLAS P. GODICI

*Acting Director of the United States Patent and Trademark Office*